(12) United States Patent
Bae et al.

(10) Patent No.: US 8,318,948 B2
(45) Date of Patent: Nov. 27, 2012

(54) FLUORENE DERIVATIVES AND ORGANIC ELECTRONIC DEVICE USING THE SAME

(75) Inventors: Jae-Soon Bae, Daejeon (KR); Dong-Hoon Lee, Seoul (KR); Dae-Woong Lee, Daejeon (KR); Sung-Kil Hong, Daejeon (KR); Hyun Nam, Seoul (KR); Chang-Hwan Kim, Jeju-si (KR)

(73) Assignee: LG Chem, Ltd., Seoul (KR)

( * ) Notice: Subject to any disclaimer, the term of this patent is extended or adjusted under 35 U.S.C. 154(b) by 588 days.

(21) Appl. No.: 12/448,044

(22) PCT Filed: Dec. 6, 2007

(86) PCT No.: PCT/KR2007/006303
§ 371 (c)(1),
(2), (4) Date: Jun. 5, 2009

(87) PCT Pub. No.: WO2008/069586
PCT Pub. Date: Jun. 12, 2008

(65) Prior Publication Data
US 2010/0071769 A1 Mar. 25, 2010

(30) Foreign Application Priority Data
Dec. 6, 2006 (KR) .................. 10-2006-0122772

(51) Int. Cl.
*C07D 293/00* (2006.01)
*C07D 417/00* (2006.01)
*B32B 9/00* (2006.01)

(52) U.S. Cl. ......... 548/100; 548/181; 428/690; 428/917
(58) Field of Classification Search .................. 548/100, 548/181; 428/690, 917
See application file for complete search history.

(56) References Cited

U.S. PATENT DOCUMENTS

| | | |
|---|---|---|
| 2005/0164034 A1 | 7/2005 | Park et al. |
| 2005/0221124 A1 | 10/2005 | Hwang et al. |
| 2006/0147747 A1 * | 7/2006 | Yamamoto et al. ........... 428/690 |
| 2007/0108892 A1 * | 5/2007 | Bae et al. ..................... 313/504 |

FOREIGN PATENT DOCUMENTS

| | | |
|---|---|---|
| WO | WO 2005-123634 A1 | 12/2005 |
| WO | WO 2006-101313 A1 | 9/2006 |

OTHER PUBLICATIONS

Srinivasan et al. Journal of Polymer Sciene, Polymer Chemistry Edition, 20(11), 3095-3105 (1982).*
Srinivasan et al., "Preparation and Properties of Polybenzimidazoles Containing Cardo Groups", Journal of Polymer Sciences: Polymer Chemistry Edition, vol. 20, 3095-3105 (1982).*
Srinivasan et al., "Preparation and Properties of Polybenzimidazoles Containing Cardo Groups", Journal of Polymer Sciences: Polymer Chemistry Edition, vol. 20, 1982, pp. 3095-3105.

* cited by examiner

*Primary Examiner* — Ling Choi
*Assistant Examiner* — Monique Peets
(74) *Attorney, Agent, or Firm* — McKenna Long & Aldridge LLP

(57) ABSTRACT

Disclosed is a novel fluorene derivative and an organic electronic device using the same. The organic electronic device has excellent efficiency, driving voltage, and a lifespan.

8 Claims, 1 Drawing Sheet

FLUORENE DERIVATIVES AND ORGANIC ELECTRONIC DEVICE USING THE SAME

TECHNICAL FIELD

The present invention relates to a novel fluorene derivative including a heteroaryl group bonded to fluorine and an organic electronic device using the same. This application claims priority from International Application No. PCT/KR2007/006303, filed on Dec. 6, 2007, and Korean Patent Application No. 10-2006-0122772 filed on Dec. 6, 2006 in the KIPO, both of which are incorporated herein by reference in their entirety.

BACKGROUND ART

An organic electronic device is an electronic device using an organic semiconductor substance, and it is required in the organic electronic device that holes and/or electrons are interchanged with each other between an electrode and an organic semiconductor substance. The organic electronic device may be classified into two types according to the operational mechanism. One type is an electronic device in which an exciton is formed in an organic material layer by photons provided from an external light source to the device, and the exciton is divided into an electron and a hole, and then the electron and the hole are transported to respective electrodes to be used as a current source (voltage source). The other type is an electronic device in which a hole and/or an electron is injected into an organic semiconductor material layer forming an interface with an electrode by applying a voltage or current to two or more electrodes, so as to allow the device to operate by means of the injected electron and/or hole.

Examples of the organic electronic device include an organic light emitting device, an organic solar cell, an organic photoconducting (OPC) drum, and an organic transistor. All the above-mentioned examples of the organic electronic device require an electron/hole injecting material, an electron/hole extraction substance, an electron/hole transport substance, or a light emitting substance in order to drive the device. Hereinafter, the organic light emitting device will be described in detail but the electron/hole injecting material, the electron/hole extraction substance, the electron/hole transport substance, or the light emitting substance of the above-mentioned organic electronic device operate in a similar mechanism.

Generally, organic light emission means that electric energy is converted into light energy by using an organic substance. An organic light emitting device using the organic light emission typically includes an anode, a cathode, and an organic layer that is interposed between the anode and the cathode. The organic layer is to have a multilayered structure made of different substances in order to improve efficiency and stability of the organic light emitting device. For example, the organic layer may be formed of a hole injection layer, a hole transport layer, a light emitting layer, an electron transport layer, and an electron injection layer. If voltage is applied to the electrodes in the organic light emitting device having the above-mentioned structure, a hole is injected into the organic material layer at an anode and an electron is injected into the organic material layer at a cathode. When the hole meets the electron, an exciton is generated, and light is generated when the exciton is converted into a bottom state. It is known that the organic light emitting device has properties such as self-light emission, high luminance, high efficiency, a low driving voltage, a wide viewing angle, high contrast, and a high-speed response.

The materials used for the organic material layer of the organic light emitting device may be classified into a light emitting material and a charge transporting material, for example, a hole injecting material, a hole transporting material, an electron transporting material, and an electron injecting material according to the type of function. The light emitting material may be classified into a blue, green, or red light emitting material and a yellow or orange light emitting material required to ensure a better natural color according to a light emitting color. Furthermore, a host/dopant system may be used as the light emitting material for the purpose of enhancing color purity and light emitting efficiency through energy transfer. This is based on a mechanism where if a dopant, which has better excellent light emitting efficiency and lower energy band interval than those of a host constituting the light emitting layer, is mixed with the light emitting layer in a small amount, an exciton that is generated from the light emitting layer is transported to the dopant to emit light at high efficiency. In this connection, since the wavelength of the host is moved toward the wavelength of the dopant, it is possible to obtain light having a desired wavelength according to the type of dopant.

In order to allow the organic light emitting device to fully exhibit the above-mentioned excellent characteristics, a material constituting the organic material layer in the device, for example, a hole injecting material, a hole transporting material, a light emitting material, an electron transporting material, and an electron injecting material should be essentially composed of a stable and efficient material. However, the development of a stable and efficient organic material layer material for the organic light emitting device has not yet been fully realized. Accordingly, the development of new materials is continuously desired. The development of such a material is equally required in the above-mentioned other organic electronic devices.

DISCLOSURE

Technical Problem

The present inventors have found a fluorene derivative having a novel structure, and also found that when an organic material layer of an organic electronic device is formed by using the novel fluorene derivative, efficiency of the device is increased, driving voltage is reduced, and stability is increased. Therefore, it is an object of the present to provide a novel fluorene derivative and an organic electronic device using the same.

Technical Solution

The present invention provides a fluorene derivative represented by Formula 1:

[Formula 1]

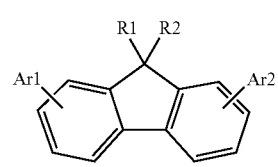

wherein R1 is a group of Formula 2:

[Formula 2]

R2 is a group of Formula 3:

[Formula 3]

wherein R3 and R4 are each independently a $C_6$ to $C_{30}$ aryl group which is substituted or unsubstituted by one or more groups selected from the group consisting of a $C_6$ to $C_{30}$ aryl group and a $C_5$ to $C_{30}$ heteroaryl group; or a $C_5$ to $C_{30}$ aliphatic heterocyclic is group or a aromatic heterocyclic group which is substituted or unsubstituted by one or more groups selected from the group consisting of a $C_6$ to $C_{30}$ aryl group and a $C_5$ to $C_{30}$ heteroaryl group, and are bonded to each other to form a condensation ring group of an aryl group, a heteroaryl group, or an aliphatic group, X is —N—Ar11, an oxygen atom, or a sulfur atom, and Ar11 is a hydrogen atom, a $C_1$ to $C_{30}$ alkyl group, a $C_6$ to $C_{30}$ aryl group, or a $C_5$ to $C_{30}$ heteroaryl group, and preferably —N-phenyl or a sulfur atom, L1 is a direct bond, or selected from the group consisting of a $C_6$ to $C_{30}$ arylene group and a $C_5$ to $C_{30}$ heteroarylene group, and Ar1, Ar2, Ar3, Ar4, Ar5, Ar6 and Ar7 are the same or different, are each independently hydrogen; halogen; an amino group; a nitrile group; a nitro group; a $C_1$ to $C_{30}$ alkyl group; a $C_2$ to $C_{40}$ alkenyl group; a $C_6$ to $C_{30}$ aryl group which is substituted or unsubstituted by one or more groups selected from the group consisting of halogen, an amino group, a nitrile group, a nitro group, a $C_1$ to $C_{30}$ alkyl group, a $C_2$ to $C_{40}$ alkenyl group, a $C_1$ to $C_{40}$ alkoxy group, a $C_3$ to $C_{30}$ cycloalkyl group, a $C_3$ to $C_{30}$ heterocycloalkyl group, a $C_6$ to $C_{30}$ aryl group, and a $C_5$ to $C_{36}$ heteroaryl group; a $C_5$ to $C_{30}$ heterocyclic group which is substituted or unsubstituted by one or more groups selected from the group consisting of halogen, an amino group, a nitrile group, a nitro group, a $C_1$ to $C_{30}$ alkyl group, a $C_2$ to $C_{40}$ alkenyl group, a $C_1$ to $C_{40}$ alkoxy group, a $C_3$ to $C_{30}$ cycloalkyl group, a $C_3$ to $C_{30}$ heterocycloalkyl group, a $C_6$ to $C_{30}$ aryl group, and a $C_5$ to $C_{30}$ heteroaryl group; a $C_6$ to $C_{30}$ arylamino group which is substituted or unsubstituted by one or more groups selected from the group consisting of halogen, an amino group, a nitrile group, a nitro group, a $C_1$ to $C_{30}$ alkyl group, a $C_2$ to $C_{40}$ alkenyl group, a $C_1$ to $C_{40}$ alkoxy group, a $C_3$ to $C_{30}$ cycloalkyl group, a $C_3$ to $C_{30}$ heterocycloalkyl group, a $C_6$ to $C_{30}$ aryl group, and a $C_5$ to $C_{30}$ heteroaryl group; or a $C_5$ to $C_{30}$ heteroarylamino group which is substituted or unsubstituted by one or more groups selected from the group consisting of halogen, an amino group, a nitrile group, a nitro group, a $C_1$ to $C_{30}$ alkyl group, a $C_2$ to $C_{40}$ alkenyl group, a $C_1$ to $C_{40}$ alkoxy group, a $C_3$ to $C_{30}$ cycloalkyl group, a $C_3$ to $C_{30}$ heterocycloalkyl group, a $C_6$ to $C_{30}$ aryl group, and a $C_5$ to $C_{30}$ heteroaryl group.

Furthermore, the present invention provides an organic electronic device which includes a first electrode, a second electrode, and an organic material layer interposed between the first electrode and the second electrode and containing the fluorene derivative.

Advantageous Effects

A novel fluorene derivative according to the present invention may be used as a material of an organic material layer of an organic electronic device such as an organic light emitting device. An organic electronic device using the fluorene derivative according to the present invention has excellent efficiency, driving voltage, and life span.

Figure 1:
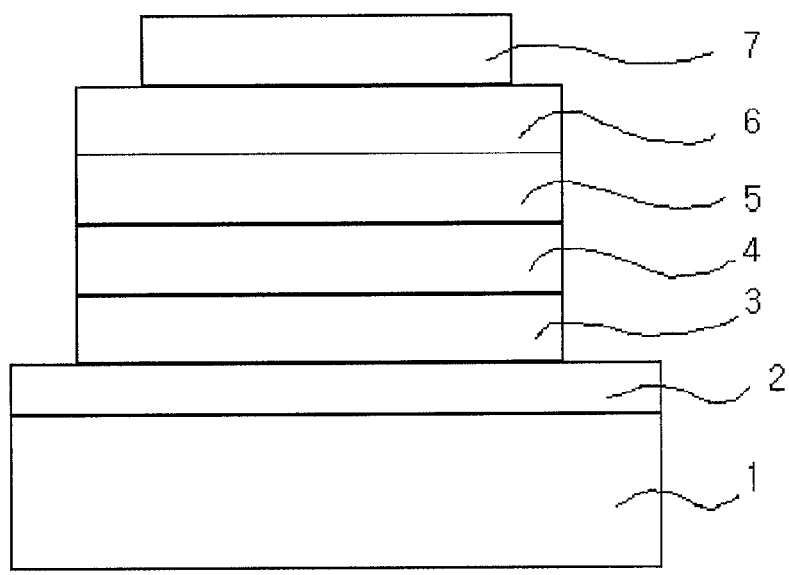
FIG. 1 is a view illustrating an exemplary structure of an organic light emitting device according to the present invention.
Figure 2:
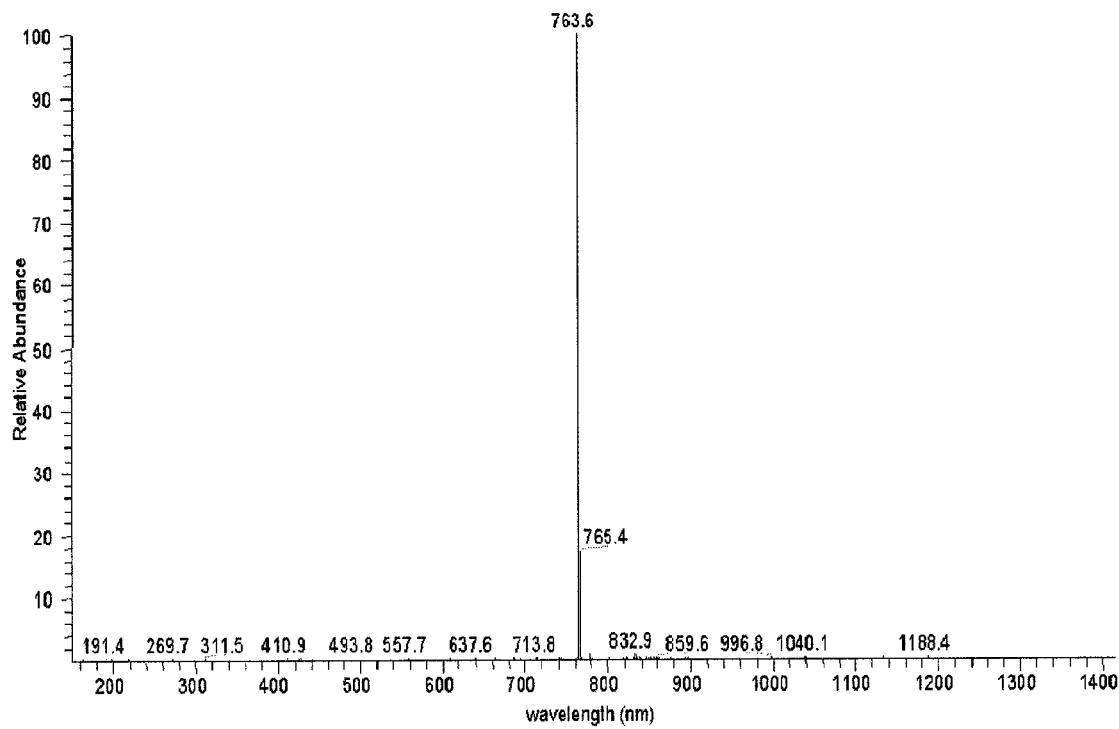
FIG. 2 illustrates a mass spectrum of a compound of Formula 1-5 which is produced in Example 1 of the present invention.

NUMERAL REFERENCES 1. substrate
2. anode
3. hole injection layer
4. hole transport layer
5. organic light emitting layer
6. electron transport layer
7. cathode

BEST MODE

Hereinafter, substituent groups used in the present invention will be described in detail.

Preferable examples of an alkenyl group include an alkenyl group having 2 to 40 carbon atoms, and specific examples of the alkenyl group include, but are not limited to, an alkenyl group which is substituted by an aryl group such as a stylbenzyl group and a styrenyl group.

Preferable examples of an alkoxy group include, but are not limited to, an alkoxy group having 1 to 40 carbon atoms.

Examples of the aryl group include, but are not limited to, a phenyl group, a naphthyl group, an anthracenyl group, a biphenyl group, a pyrenyl group, a perylenyl group, and a derivative thereof.

Examples of the arylamino group include, but are not limited to, a phenylamino group, a naphthylamino group, a biphenylamino group, an anthracenylamino group, a 3-methyl-phenylamino group, a 4-methyl-naphthylamino group, a 2-methyl-biphenylamino group, a 9-methyl-anthracenylamino group, a diphenyl amino group, a phenylnaphthylamino group, a ditolylamino group, a phenyltolylamino group, a carbazolylamino group, and a triphenylamino group.

Examples of the heterocyclic group include, but are not limited to, a pyridyl group, a bipyridyl group, a triazinyl group, an acridinyl group, a thienyl group, a furyl group, an imidazolyl group, an oxazolyl group, a thiazolyl group, a triazolyl group, a quinolyl group, and an isoquinolyl group.

Examples of the halogen group include, but are not limited to, fluorine, chlorine, bromine, and iodine.

In Formula 1, Ar1 and Ar2 are each independently hydrogen; an amine group; an alkenyl group; an aryl group which is selected from the group consisting of a phenyl group, a naphthyl group, a binaphthyl group, an anthracenyl group, a biphenyl group, a pyrenyl group, and a perylenyl group; or a heteroaryl group which is selected from the group consisting of a pyridyl group, a bipyridyl group, a triazinyl group, a thienyl group, an imidazolyl group, an oxazolyl group, a thiazolyl group, a triazolyl group, a quinolyl group, and an isoquinolyl group, but are not limited thereto.

In Formula 2, L1 may be a direct bond; or an aryl group which is selected from the group consisting of a phenyl group, a biphenyl group, a naphthyl group, a pyrenyl group, and a perylenyl group, and preferably a phenyl group which is substituted or unsubstituted by one or more naphthyl groups, phenyl groups, or naphthyl groups, or a naphthyl group which is substituted or unsubstituted by one or more naphthyl groups, phenyl groups, or naphthyl groups, but are not limited thereto.

In Formula 3, Ar3, Ar4, Ar5, Ar6, and Ar7 are each independently hydrogen; a methyl group; an ethyl group; and an aryl group which is selected from the group consisting of a phenyl group, a naphthyl group, an anthracenyl group, a biphenyl group, a pyrenyl group, and a perylenyl group, but are not limited thereto. More preferably, Ar3, Ar4, Ar5, Ar6, and Ar7 may be each independently hydrogen.

The following structural formulae are specific examples of the compound of Formula 1, but the scope of the present invention is not 1 imi ted thereto.

TABLE
| 화합물 | R1 | R2 | Ar1 | Ar2 |
|---|---|---|---|---|
| 1-1 | 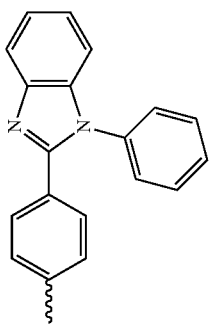 | 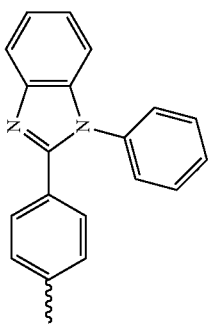 | H | H |
| 1-2 | 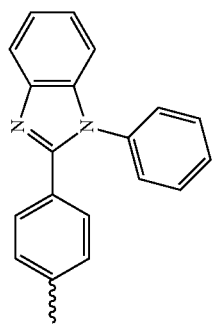 | 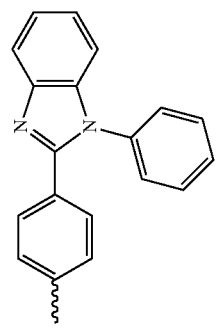 |  | 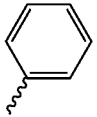 |
| 1-3 | 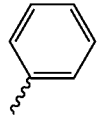 | 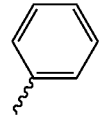 | 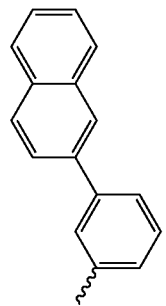 | 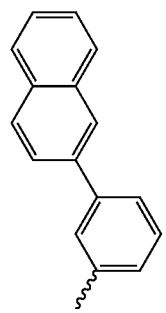 |
| 1-4 | | | | |

TABLE-continued
| 번호 | R1 | R2 | Ar1 | Ar2 |
|---|---|---|---|---|
| 1-5 | 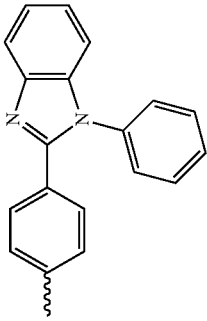 | 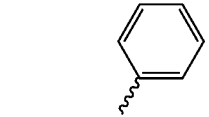 |  | 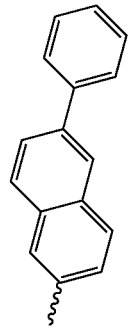 |
| 1-6 | 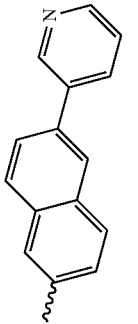 | 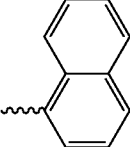 | 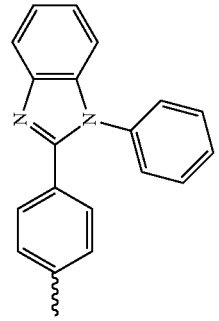 | 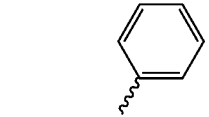 |
| 1-7 |  | 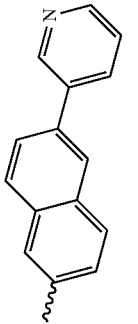 | 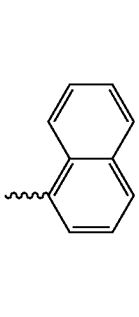 | 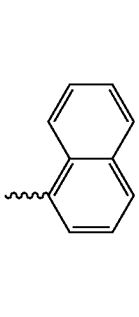 |
| 1-8 | 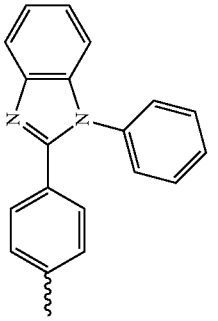 | 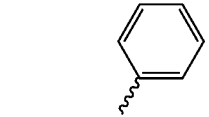 |  | 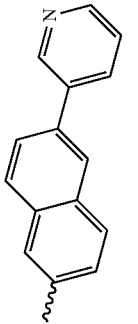 |

TABLE-continued
| 화합물 | R1 | R2 | Ar1 | Ar2 |
|---|---|---|---|---|
| 1-9 | 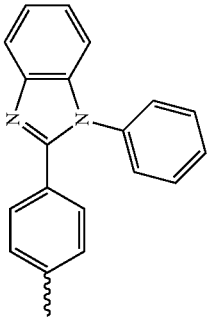 |  | 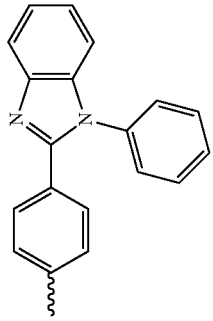 | 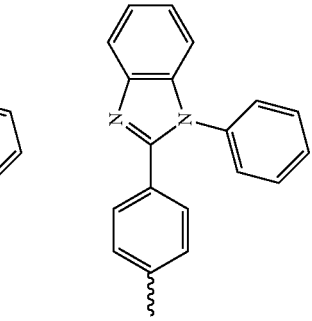 |
| 1-10 | 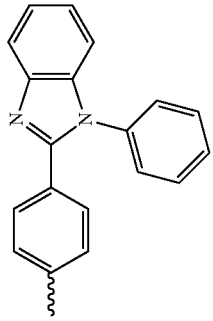 | 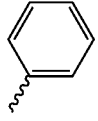 | 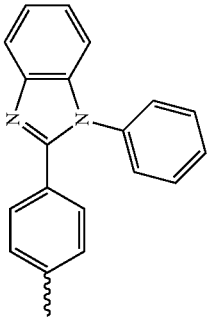 | 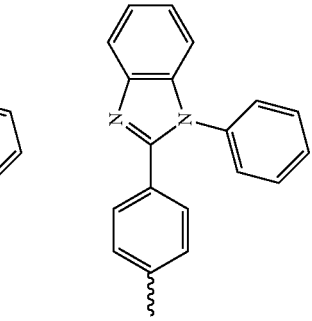 |
| 1-11 | 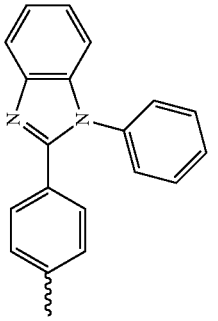 | 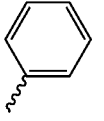 | 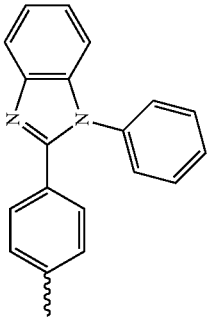 | 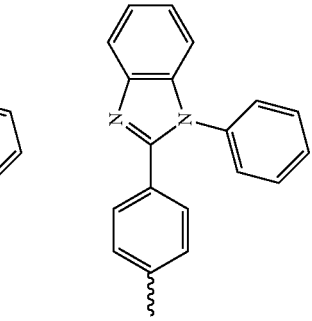 |
| 1-12 | 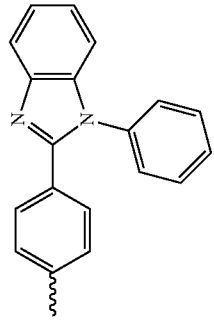 | 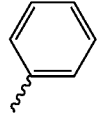 | 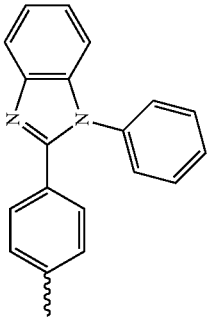 | 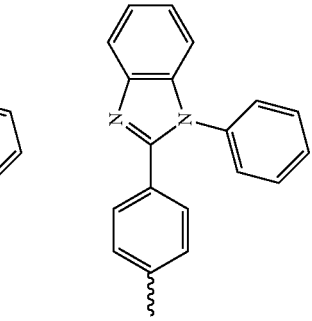 |

TABLE-continued

| 번호 | R1 | R2 | Ar1 | Ar2 |
|---|---|---|---|---|
| 1-13 | | | | |
| 1-14 | | | | |
| 1-15 | | | | |
| 1-16 | | | | |

TABLE-continued

| 번호 | R1 | R2 | Ar1 | Ar2 |
|---|---|---|---|---|
| 1-17 | benzimidazole-N-phenyl, 2-(4-phenyl) | phenyl | 2-(4-phenyl)benzothiazole | 2-(4-phenyl)benzothiazole |
| 1-18 | benzimidazole-N-phenyl, 2-(4-phenyl) | phenyl | 2-(3-phenyl)benzothiazole | 2-(3-phenyl)benzothiazole |
| 1-19 | benzimidazole-N-phenyl, 2-(4-phenyl) | phenyl | 2-pyridyl | 2-pyridyl |
| 1-20 | benzimidazole-N-phenyl, 2-(4-phenyl) | phenyl | 4-pyridyl | 4-pyridyl |

TABLE-continued
| 번호 | R1 | R2 | Ar1 | Ar2 |
|---|---|---|---|---|
| 1-21 | 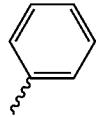 | 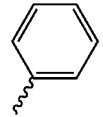 | 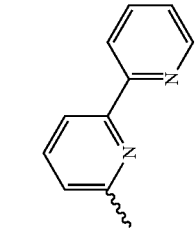 | 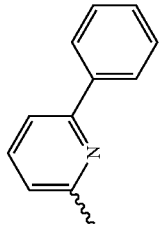 |
| 1-22 | 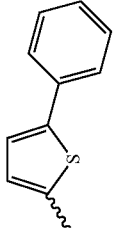 | 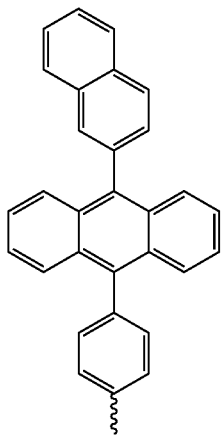 | 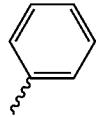 | 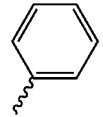 |
| 1-23 | 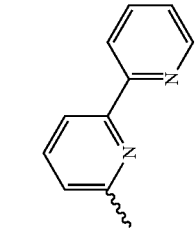 | 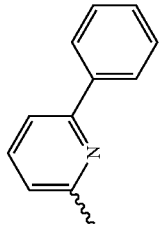 | 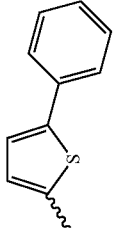 | 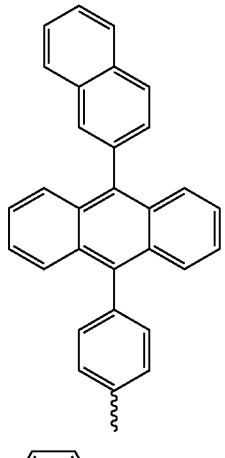 |
| 1-24 | 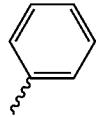 | 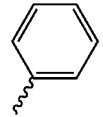 | 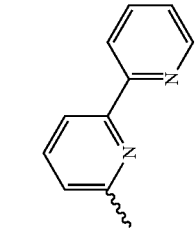 | 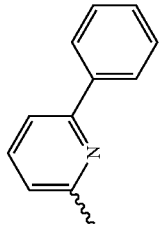 |

TABLE-continued

| 번호 | R1 | R2 | Ar1 | Ar2 |
|---|---|---|---|---|
| 2-1 | benzimidazole-phenyl | phenyl | H | H |
| 2-2 | benzimidazole-phenyl | phenyl | phenyl | phenyl |
| 2-3 | benzimidazole-phenyl | phenyl | biphenyl | biphenyl |
| 2-4 | benzimidazole-phenyl | phenyl | naphthylphenyl | naphthylphenyl |

TABLE-continued
| 번호 | R1 | R2 | Ar1 | Ar2 |
|---|---|---|---|---|
| 2-5 | 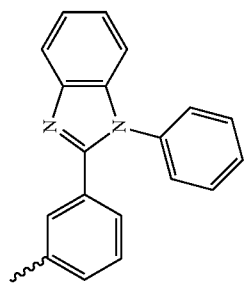 | 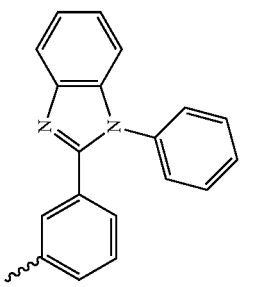 | 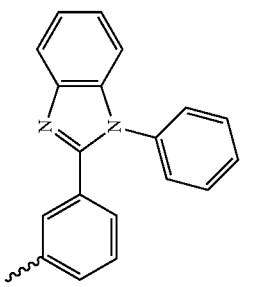 | 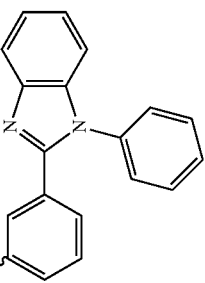 |
| 2-6 | 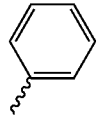 | 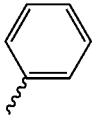 | 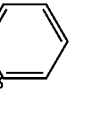 | 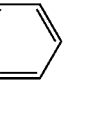 |
| 2-7 | 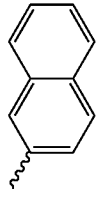 | 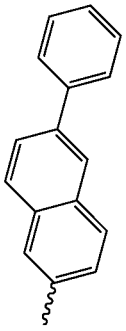 | 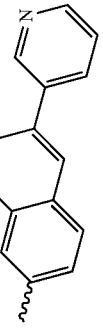 | 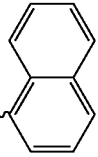 |
| 2-8 | 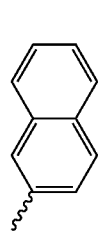 | 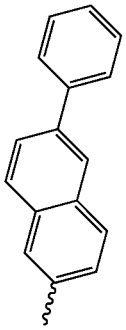 | 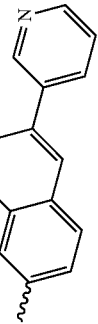 | 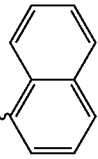 |

TABLE-continued

| 번호 | R1 | R2 | Ar1 | Ar2 |
|---|---|---|---|---|
| 2-9 | N-phenylbenzimidazol-2-yl-phenyl | phenyl | pyrenyl | pyrenyl |
| 2-10 | N-phenylbenzimidazol-2-yl-phenyl | phenyl | 10-(naphthalen-2-yl)anthracen-9-yl | 10-(naphthalen-2-yl)anthracen-9-yl |
| 2-11 | N-phenylbenzimidazol-2-yl-phenyl | phenyl | 10-(biphenyl-3-yl)anthracen-9-yl | 10-(biphenyl-3-yl)anthracen-9-yl |
| 2-12 | N-phenylbenzimidazol-2-yl-phenyl | phenyl | N-phenylbenzimidazol-2-yl-phenyl | N-phenylbenzimidazol-2-yl-phenyl |

| 번호 | R1 | R2 | Ar1 | Ar2 |
|---|---|---|---|---|
| 2-13 | benzimidazole-phenyl-phenyl | phenyl | benzimidazole-phenyl-phenyl | benzimidazole-phenyl-phenyl |
| 2-14 | benzimidazole-phenyl-phenyl | phenyl | benzimidazole-phenyl | benzimidazole-phenyl |
| 2-15 | benzimidazole-phenyl-phenyl | phenyl | benzimidazole-phenyl | benzimidazole-phenyl |
| 2-16 | benzimidazole-phenyl-phenyl | phenyl | benzothiazole | benzothiazole |

TABLE-continued

| 번호 | R1 | R2 | Ar1 | Ar2 |
|---|---|---|---|---|
| 2-17 | benzimidazole-N-phenyl, 2-(3-phenyl) | phenyl | 2-(4-phenyl)benzothiazole | 2-(4-phenyl)benzothiazole |
| 2-18 | benzimidazole-N-phenyl, 2-(3-phenyl) | phenyl | 2-(3-phenyl)benzothiazole | 2-(3-phenyl)benzothiazole |
| 2-19 | benzimidazole-N-phenyl, 2-(3-phenyl) | phenyl | 2-pyridyl | 2-pyridyl |
| 2-20 | benzimidazole-N-phenyl, 2-(3-phenyl) | phenyl | 4-pyridyl | 4-pyridyl |

TABLE-continued

| 번호 | R1 | R2 | Ar1 | Ar2 |
|---|---|---|---|---|
| 2-21 | benzimidazole-phenyl on phenyl | phenyl | 2-phenylpyridine | 2-phenylpyridine |
| 2-22 | benzimidazole-phenyl on phenyl | phenyl | 2-phenylpyridine | 2-phenylpyridine |
| 2-23 | benzimidazole-phenyl on phenyl | phenyl | 2-phenylthiophene | 2-phenylthiophene |
| 2-24 | benzimidazole-phenyl on phenyl | phenyl | 9-naphthyl-10-phenyl-anthracene | 9-naphthyl-10-phenyl-anthracene |

TABLE-continued

| 번호 | R1 | R2 | Ar1 | Ar2 |
|---|---|---|---|---|
| 3-1 | 4-biphenylyl-benzimidazole(N-phenyl) | phenyl | H | H |
| 3-2 | 4-biphenylyl-benzimidazole(N-phenyl) | phenyl | phenyl | phenyl |
| 3-3 | 4-biphenylyl-benzimidazole(N-phenyl) | phenyl | biphenyl | biphenyl |
| 3-4 | 4-biphenylyl-benzimidazole(N-phenyl) | phenyl | 3-(2-naphthyl)phenyl | 3-(2-naphthyl)phenyl |

TABLE-continued

| 화학식 | R1 | R2 | Ar1 | Ar2 |
|---|---|---|---|---|
| 3-5 | | | | |
| 3-6 | | | | |
| 3-7 | | | | |
| 3-8 | | | | |

TABLE-continued
| 번호 | R1 | R2 | Ar1 | Ar2 |
|---|---|---|---|---|
| 3-9 | 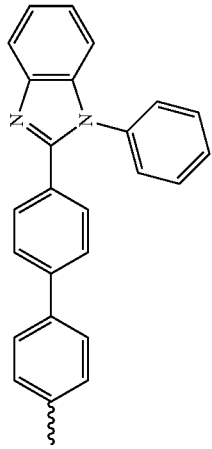 | 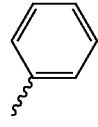 | 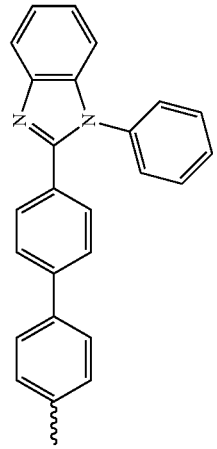 | 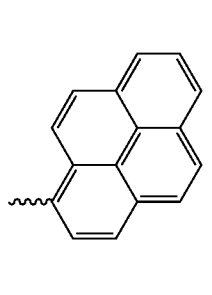 |
| 3-10 | 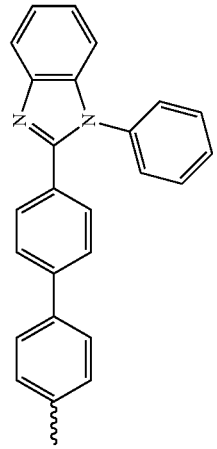 | 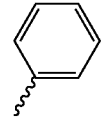 | 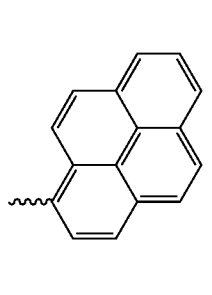 | 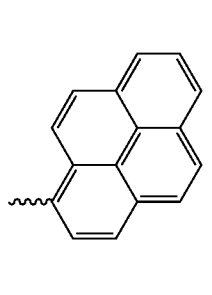 |
| 3-11 | 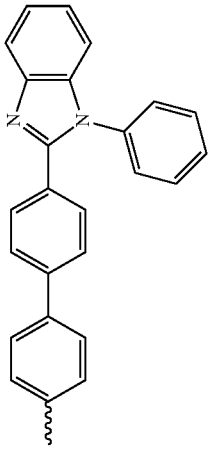 | 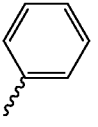 | 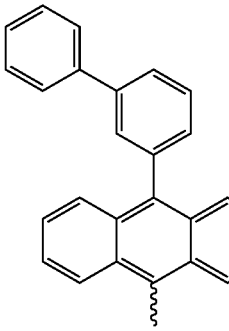 | 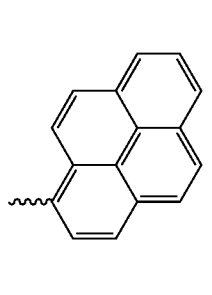 |
| 3-12 | 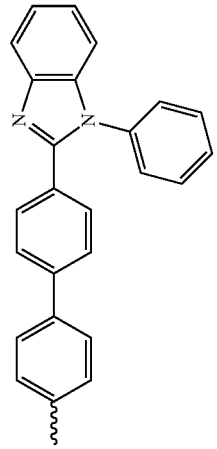 | 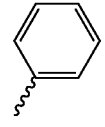 | 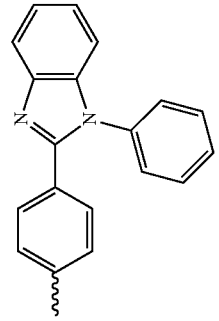 | 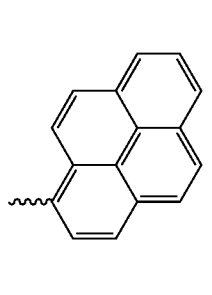 |

TABLE-continued
| 번호 | R1 | R2 | Ar1 | Ar2 |
|---|---|---|---|---|
| 3-13 |  | 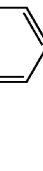 | 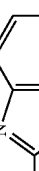 | 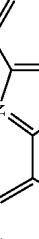 |
| 3-14 |  |  |  | 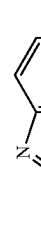 |
| 3-15 |  |  | 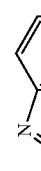 | 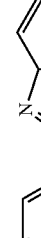 |
| 3-16 |  | 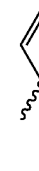 |  | 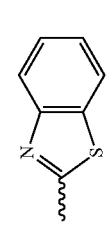 |

TABLE-continued

| 번호 | R1 | R2 | Ar1 | Ar2 |
|---|---|---|---|---|
| 3-17 | benzimidazole-N-phenyl on biphenyl | phenyl | 2-(4-phenyl)benzothiazole | 2-(4-phenyl)benzothiazole |
| 3-18 | benzimidazole-N-phenyl on biphenyl | phenyl | 2-(3-phenyl)benzothiazole | 2-(3-phenyl)benzothiazole |
| 3-19 | benzimidazole-N-phenyl on biphenyl | phenyl | 2-pyridyl | 2-pyridyl |
| 3-20 | benzimidazole-N-phenyl on biphenyl | phenyl | 4-pyridyl | 4-pyridyl |

TABLE-continued
| 번호 | R1 | R2 | Ar1 | Ar2 |
|---|---|---|---|---|
| 3-21 | 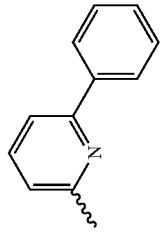 | 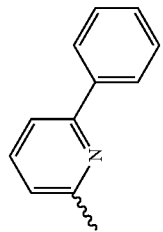 | 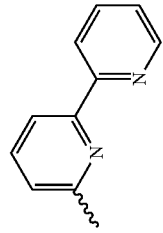 | 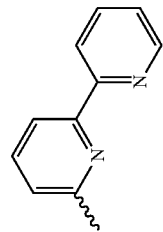 |
| 3-22 | 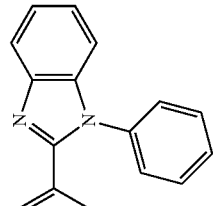 | 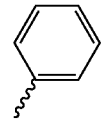 | 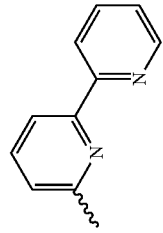 | 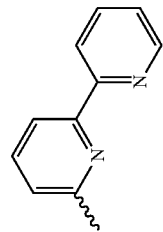 |
| 3-23 | 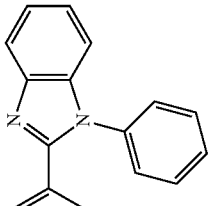 | 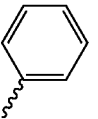 | 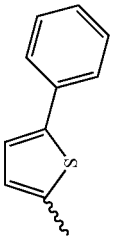 | 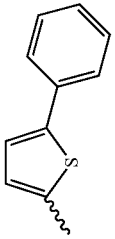 |
| 3-24 | 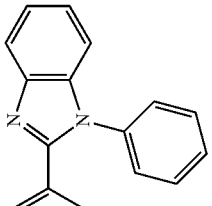 | 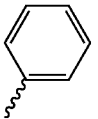 | 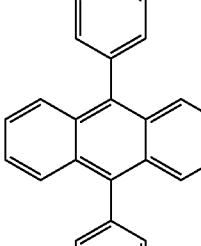 | 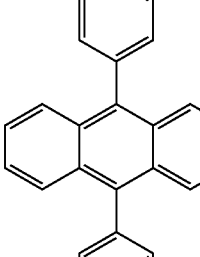 |

TABLE-continued

| 번호 | R1 | R2 | Ar1 | Ar2 |
|---|---|---|---|---|
| 4-1 | (naphthalene-naphthalene-phenyl with benzimidazole-phenyl) | phenyl | H | H |
| 4-2 | (naphthalene-naphthalene-phenyl with benzimidazole-phenyl) | phenyl | phenyl | phenyl |
| 4-3 | (naphthalene-naphthalene-phenyl with benzimidazole-phenyl) | phenyl | biphenyl | biphenyl |

TABLE-continued

| 번호 | R1 | R2 | Ar1 | Ar2 |
|---|---|---|---|---|
| 4-4 | (benzimidazole-phenyl with naphthyl-naphthyl-phenyl substituent) | phenyl | 3-naphthylphenyl | 3-naphthylphenyl |
| 4-5 | (benzimidazole-phenyl with naphthyl-naphthyl-phenyl substituent) | phenyl | naphthyl | naphthyl |
| 4-6 | (benzimidazole-phenyl with naphthyl-naphthyl-phenyl substituent) | phenyl | phenylnaphthyl | phenylnaphthyl |

TABLE-continued

| 번호 | R1 | R2 | Ar1 | Ar2 |
|---|---|---|---|---|
| 4-7 | | | | |
| 4-8 | | | | |
| 4-9 | | | | |

TABLE-continued

| 화합물 | R1 | R2 | Ar1 | Ar2 |
|---|---|---|---|---|
| 4-10 | | | | |
| 4-11 | | | | |
| 4-12 | | | | |

TABLE-continued
| 화합물 | R1 | R2 | Ar1 | Ar2 |
|---|---|---|---|---|
| 4-13 | 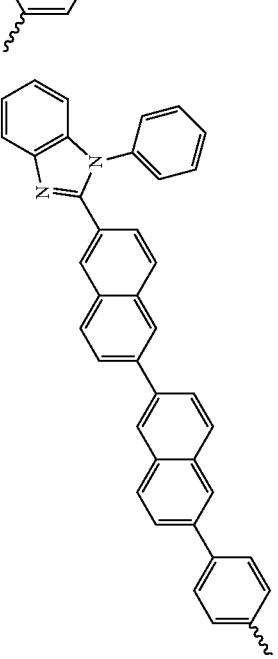 | 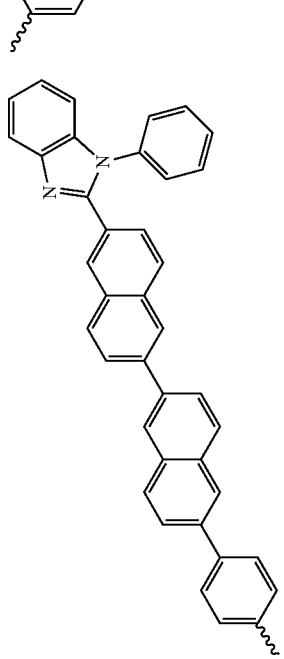 | 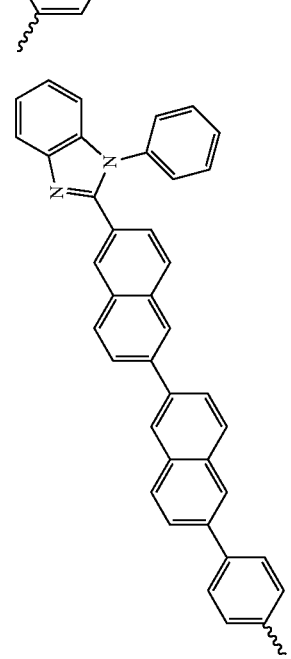 | 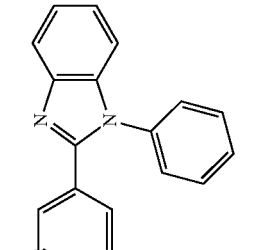 |
| 4-14 | 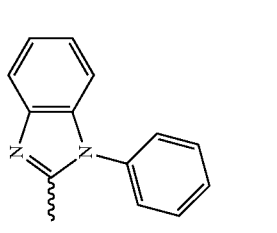 | 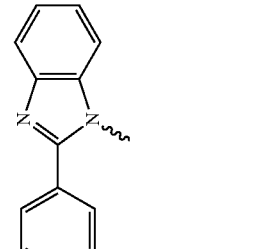 | 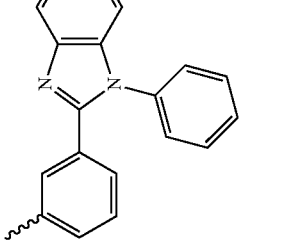 | 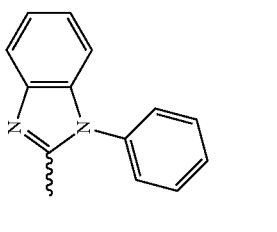 |
| 4-15 | 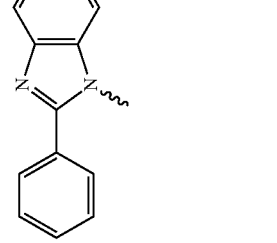 | 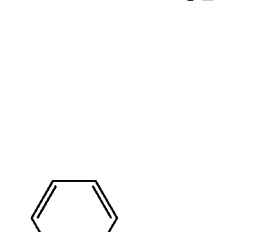 | 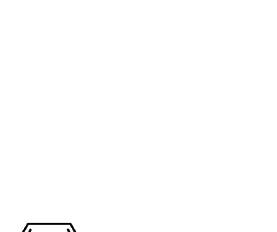 | 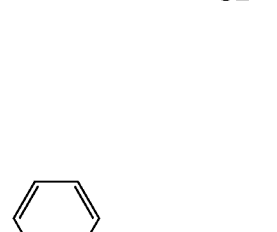 |

TABLE-continued

| 화합물 | R1 | R2 | Ar1 | Ar2 |
|---|---|---|---|---|
| 4-16 | | | | |
| 4-17 | | | | |
| 4-18 | | | | |

| 번호 | R1 | R2 | Ar1 | Ar2 |
|---|---|---|---|---|
| 4-19 | 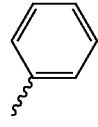 | 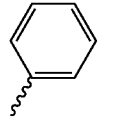 | 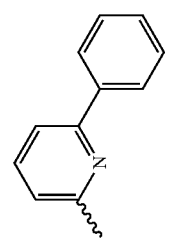 | 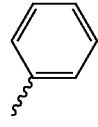 |
| 4-20 | 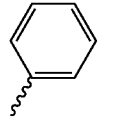 | 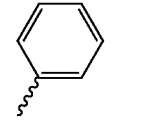 | 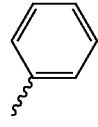 | 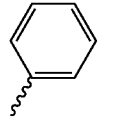 |
| 4-21 | 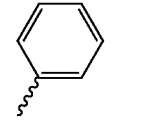 | | | |

TABLE-continued
| 번호 | R1 | R2 | Ar1 | Ar2 |
|---|---|---|---|---|
| 4-22 | 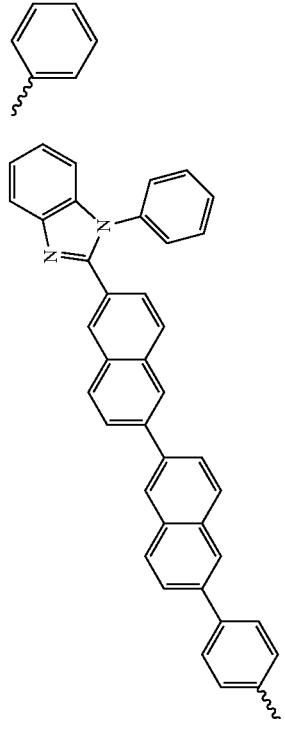 | 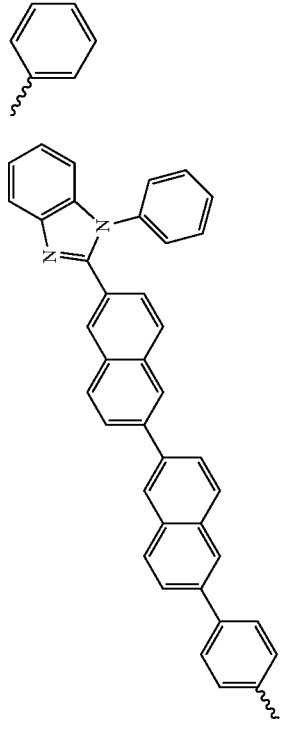 | 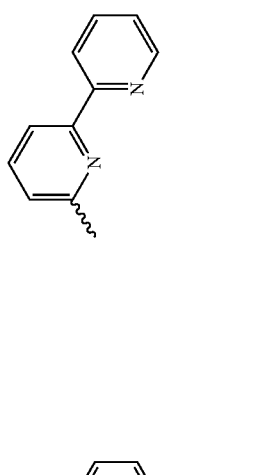 | 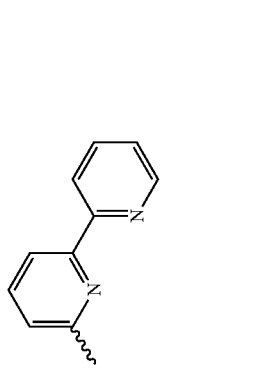 |
| 4-23 | 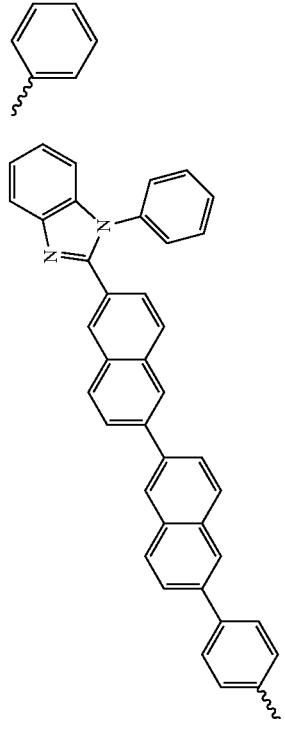 | 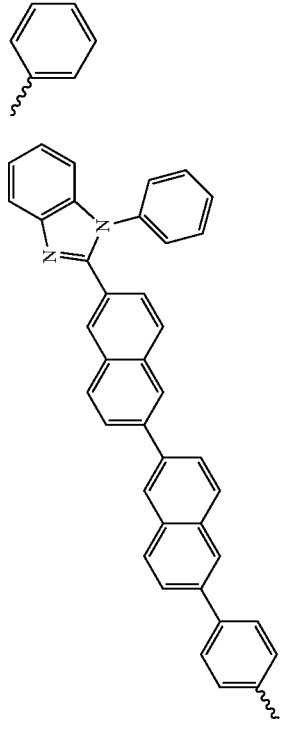 | 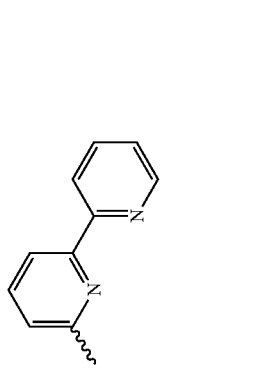 | 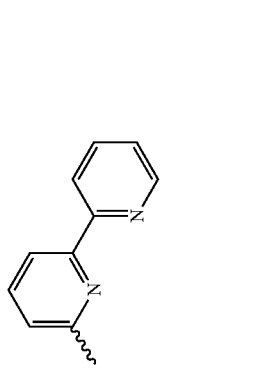 |
| 4-24 | 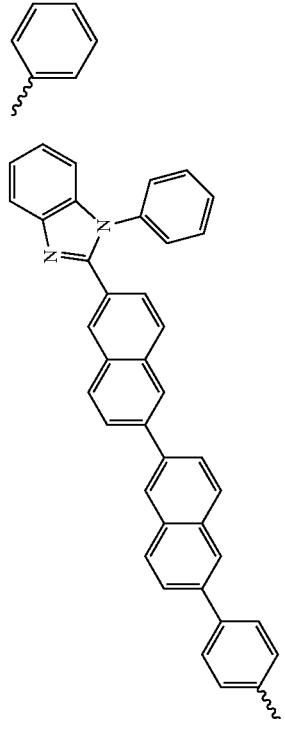 | 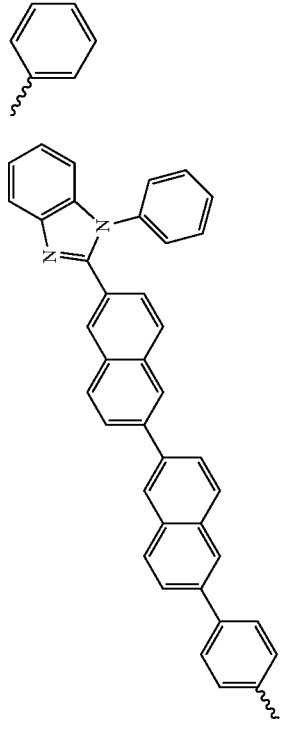 | 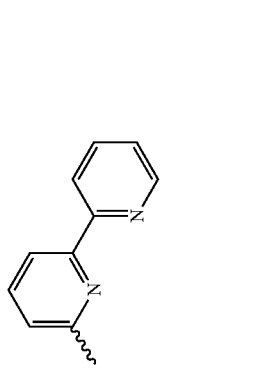 | 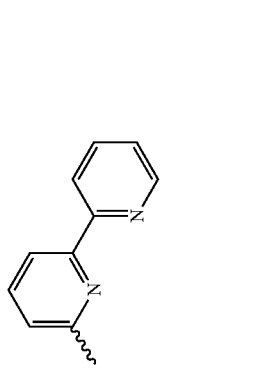 |

TABLE-continued
| 번호 | R1 | R2 | Ar1 | Ar2 |
|---|---|---|---|---|
| 5-1 | 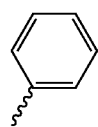 | 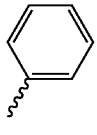 | H | H |
| 5-2 | 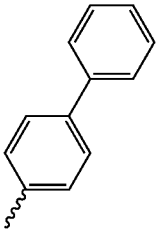 | 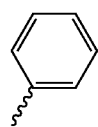 |  | 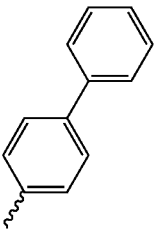 |
| 5-3 | 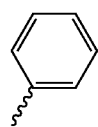 | 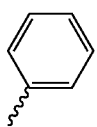 | 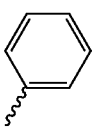 | 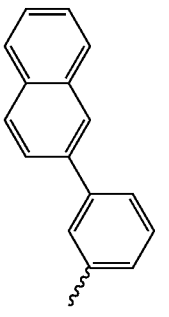 |
| 5-4 | 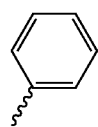 | 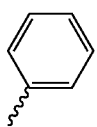 | 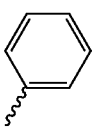 | 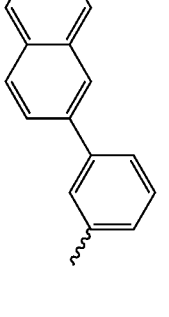 |

TABLE-continued

| 번호 | R1 | R2 | Ar1 | Ar2 |
|---|---|---|---|---|
| 5-5 | (1-phenyl-benzimidazol-2-yl, 10-phenyl-anthracen-9-yl) | phenyl | naphthalen-2-yl | naphthalen-2-yl |
| 5-6 | (1-phenyl-benzimidazol-2-yl, 10-phenyl-anthracen-9-yl) | phenyl | 6-phenyl-naphthalen-2-yl | 6-phenyl-naphthalen-2-yl |
| 5-7 | (1-phenyl-benzimidazol-2-yl, 10-phenyl-anthracen-9-yl) | phenyl | 6-(pyridin-3-yl)-naphthalen-2-yl | 6-(pyridin-3-yl)-naphthalen-2-yl |
| 5-8 | (1-phenyl-benzimidazol-2-yl, 10-phenyl-anthracen-9-yl) | phenyl | naphthalen-1-yl | naphthalen-1-yl |

TABLE-continued

| 번호 | R1 | R2 | Ar1 | Ar2 |
|---|---|---|---|---|
| 5-9 | benzimidazole-phenylanthracene | phenyl | pyrene | pyrene |
| 5-10 | benzimidazole-phenylanthracene | phenyl | 2-naphthyl-anthracene | 2-naphthyl-anthracene |
| 5-11 | benzimidazole-phenylanthracene | phenyl | biphenyl-anthracene | biphenyl-anthracene |
| 5-12 | benzimidazole-phenylanthracene | phenyl | phenyl-N-phenylbenzimidazole | phenyl-N-phenylbenzimidazole |

| 번호 | R1 | R2 | Ar1 | Ar2 |
|---|---|---|---|---|
| 5-13 | 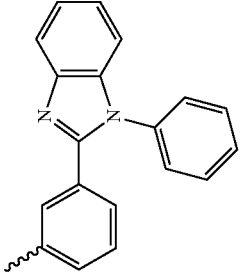 | 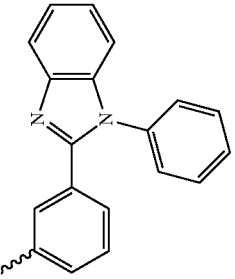 | 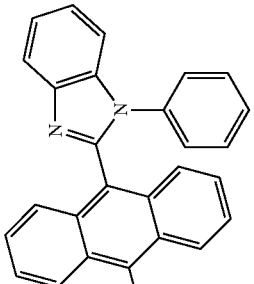 | 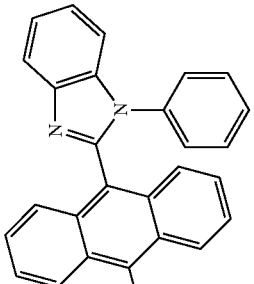 |
| 5-14 | 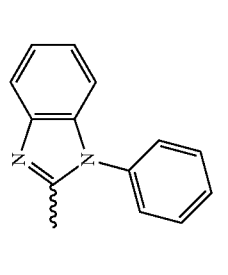 | 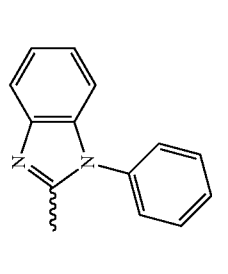 | 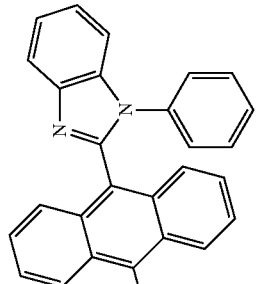 | 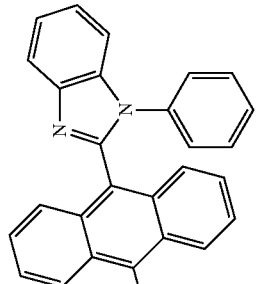 |
| 5-15 | 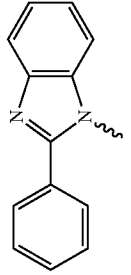 | 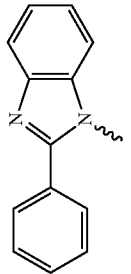 | 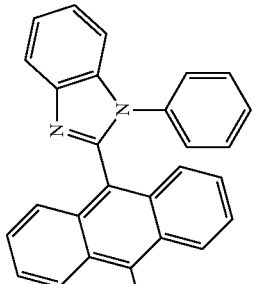 | 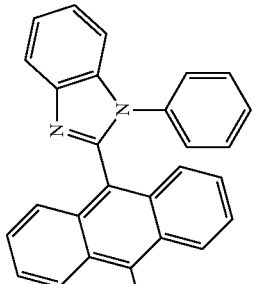 |
| 5-16 | 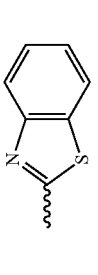 | 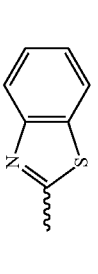 | 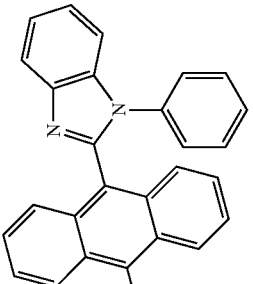 | 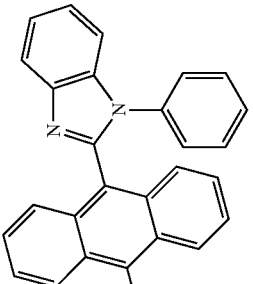 |

| 번호 | R1 | R2 | Ar1 | Ar2 |
|---|---|---|---|---|
| 5-17 | (N-phenylbenzimidazol-2-yl)-(10-phenylanthracen-9-yl) | phenyl | 2-(4-phenyl)benzothiazole | 2-(4-phenyl)benzothiazole |
| 5-18 | (N-phenylbenzimidazol-2-yl)-(10-phenylanthracen-9-yl) | phenyl | 2-(3-phenyl)benzothiazole | 2-(3-phenyl)benzothiazole |
| 5-19 | (N-phenylbenzimidazol-2-yl)-(10-phenylanthracen-9-yl) | phenyl | 2-pyridyl | 2-pyridyl |
| 5-20 | (N-phenylbenzimidazol-2-yl)-(10-phenylanthracen-9-yl) | phenyl | 4-pyridyl | 4-pyridyl |

| 번호 | R1 | R2 | Ar1 | Ar2 |
|---|---|---|---|---|
| 5-21 | 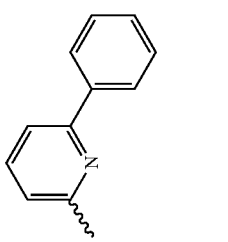 | 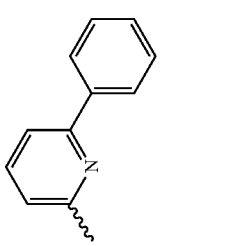 | 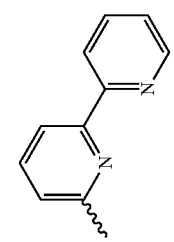 | 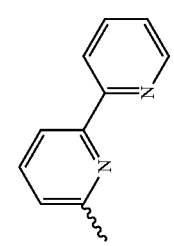 |
| 5-22 | 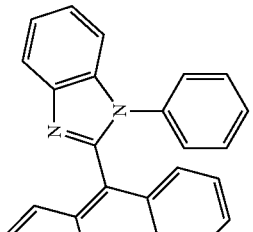 | 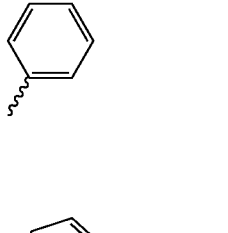 | 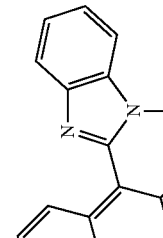 | 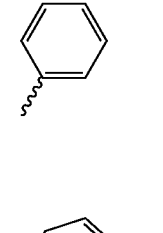 |
| 5-23 | 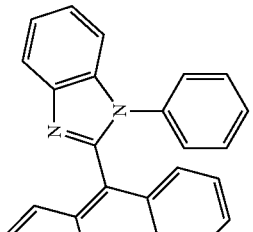 | 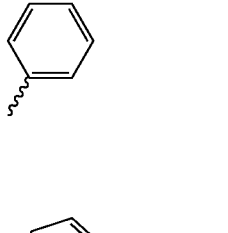 | 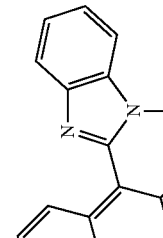 | 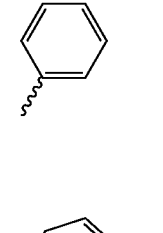 |
| 5-24 | 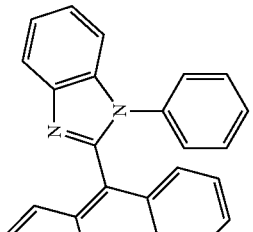 | 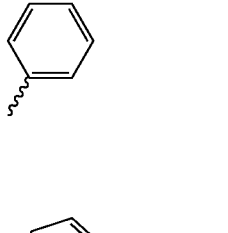 | 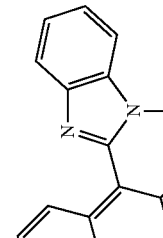 | 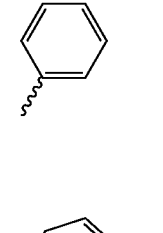 |

| 번호 | R1 | R2 | Ar1 | Ar2 |
|---|---|---|---|---|
| 6-1 | ![](anthracene-phenyl-benzimidazole) | phenyl | H | H |
| 6-2 | ![](anthracene-phenyl-benzimidazole) | phenyl | phenyl | phenyl |
| 6-3 | ![](anthracene-phenyl-benzimidazole) | phenyl | biphenyl | biphenyl |

TABLE-continued
| 번호 | R1 | R2 | Ar1 | Ar2 |
|---|---|---|---|---|
| 6-4 | 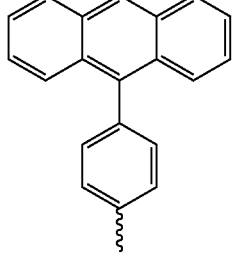 | 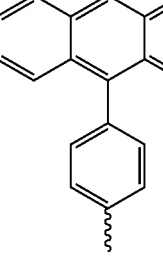 | 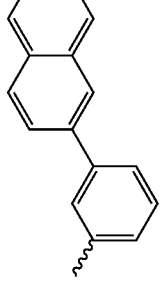 | 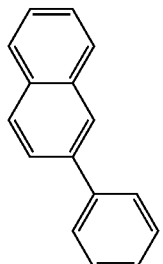 |
| 6-5 | 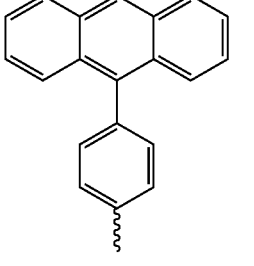 | 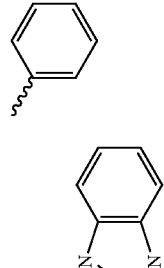 | 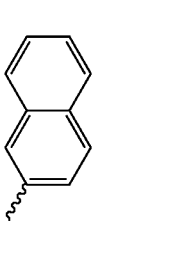 | 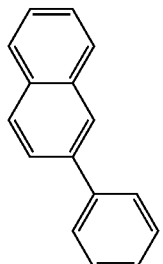 |
| 6-6 | 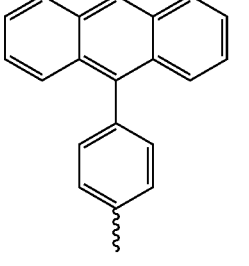 | 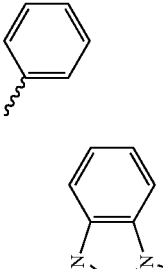 | 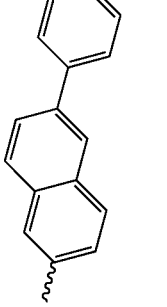 | 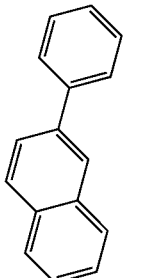 |

| 예 | R1 | R2 | Ar1 | Ar2 |
|---|---|---|---|---|
| 6-7 | 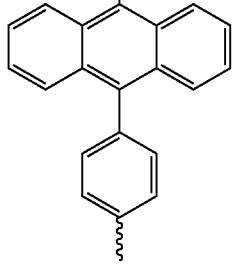 | 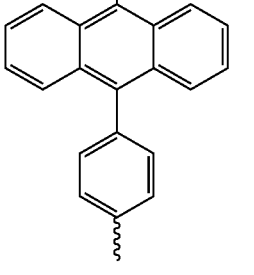 | 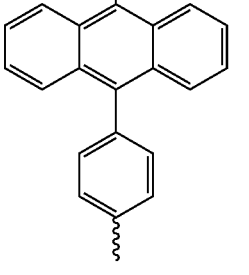 | 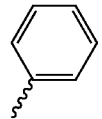 |
| 6-8 | 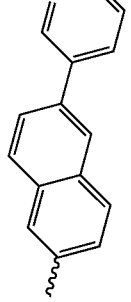 | 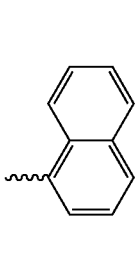 | 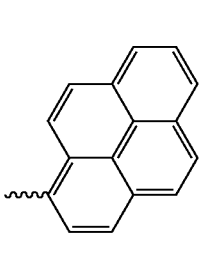 | 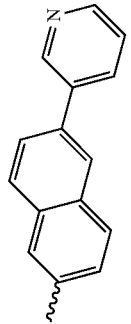 |
| 6-9 | 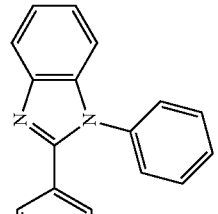 | 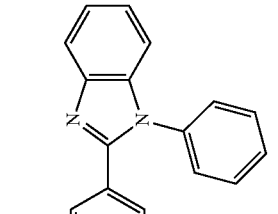 | 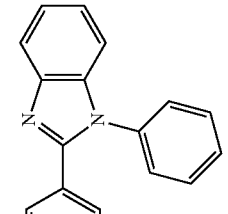 | 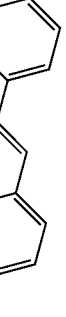 |

TABLE-continued

| 번호 | R1 | R2 | Ar1 | Ar2 |
|---|---|---|---|---|
| 6-10 | | | | |
| 6-11 | | | | |
| 6-12 | | | | |

TABLE-continued
| 번호 | R1 | R2 | Ar1 | Ar2 |
|---|---|---|---|---|
| 6-13 | 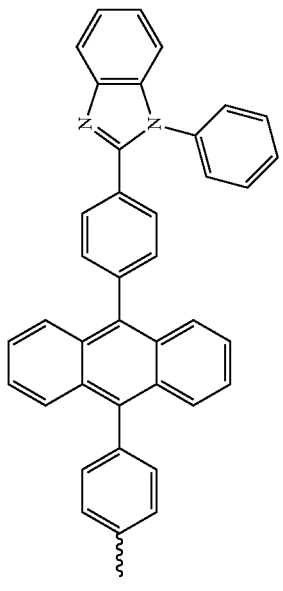 | 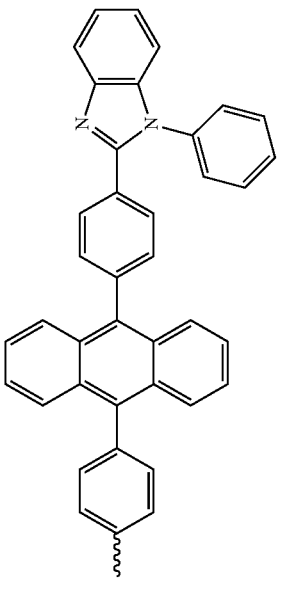 | 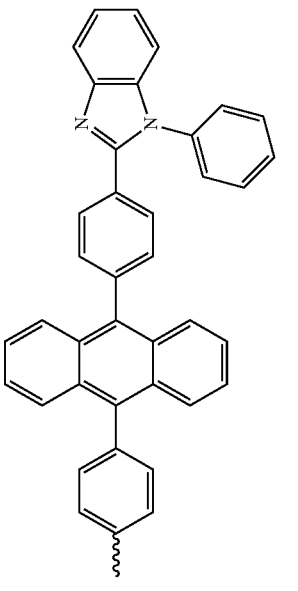 | 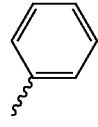 |
| 6-14 | 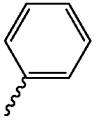 |  | 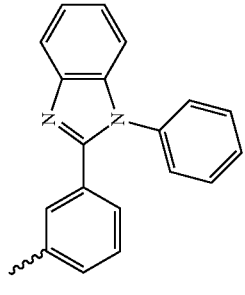 | 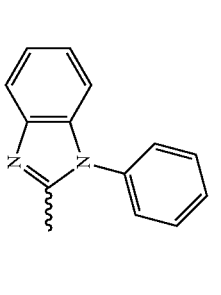 |
| 6-15 | 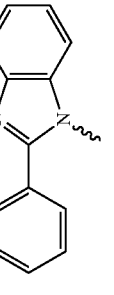 | 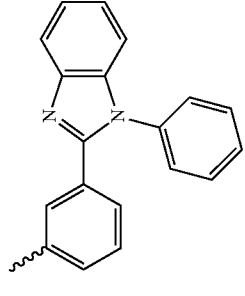 | 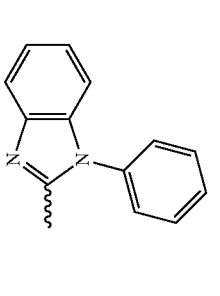 | 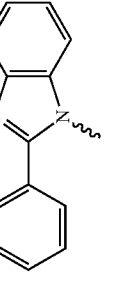 |

TABLE-continued

| 번호 | R1 | R2 | Ar1 | Ar2 |
|---|---|---|---|---|
| 6-16 | | | | |
| 6-17 | | | | |
| 6-18 | | | | |

TABLE-continued

| 번호 | R1 | R2 | Ar1 | Ar2 |
|---|---|---|---|---|
| 6-19 | (10-(4-phenyl)-9-(4-phenyl)anthracene with 1-phenyl-benzimidazol-2-yl) | phenyl | pyridin-2-yl | pyridin-2-yl |
| 6-20 | (10-(4-phenyl)-9-(4-phenyl)anthracene with 1-phenyl-benzimidazol-2-yl) | phenyl | pyridin-4-yl | pyridin-4-yl |
| 6-21 | (10-(4-phenyl)-9-(4-phenyl)anthracene with 1-phenyl-benzimidazol-2-yl) | phenyl | 2-phenylpyridin-6-yl | 2-phenylpyridin-6-yl |

| 번호 | R1 | R2 | Ar1 | Ar2 |
|---|---|---|---|---|
| 6-22 | 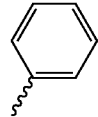 | 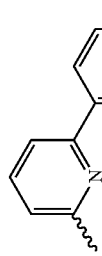 | 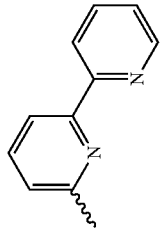 | 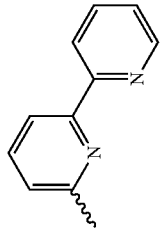 |
| 6-23 | 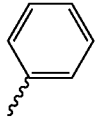 | 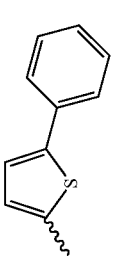 | 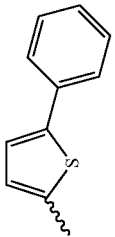 | 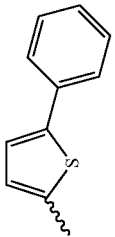 |
| 6-24 | 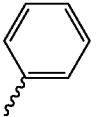 | 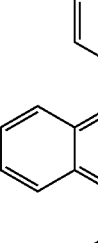 | 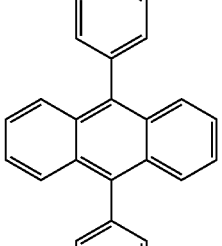 | 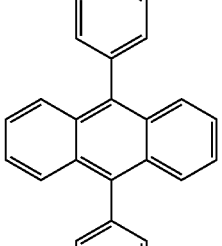 |
| 7-1 | 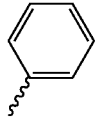 |  | H | H |

TABLE-continued
| 번호 | R1 | R2 | Ar1 | Ar2 |
|---|---|---|---|---|
| 7-2 | 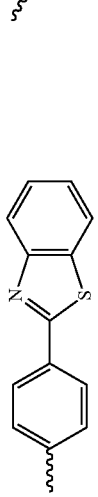 | 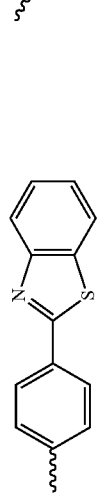 | 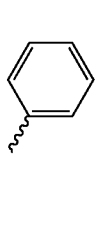 | 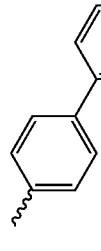 |
| 7-3 |  | 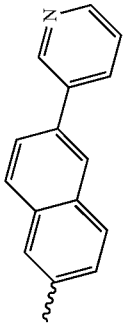 | 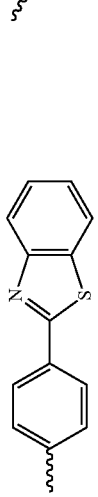 | 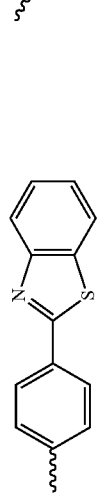 |
| 7-4 | 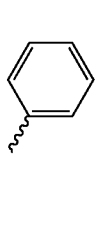 | 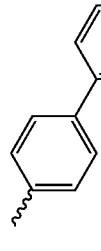 |  | 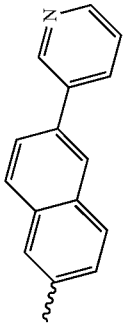 |
| 7-5 | 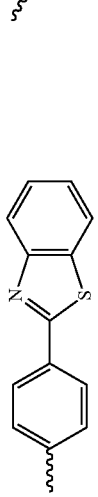 | 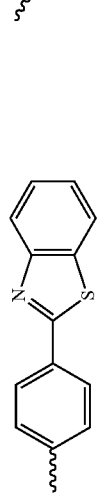 | 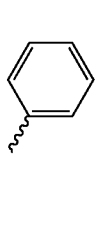 | 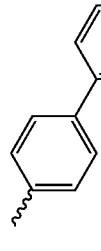 |
| 7-6 |  | 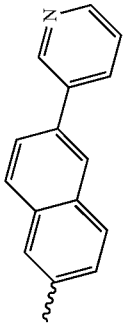 | 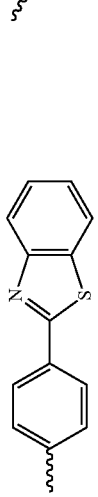 | 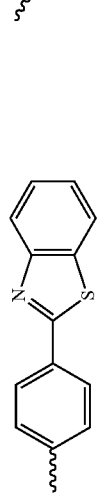 |
| 7-7 | 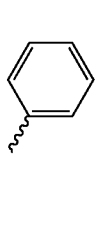 | 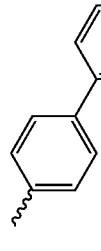 |  | 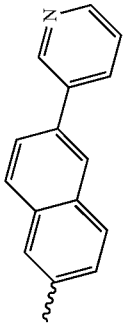 |
| 7-8 | 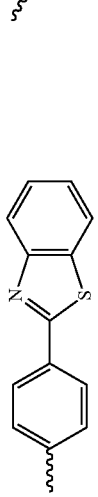 | 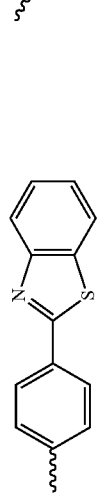 | 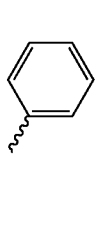 | 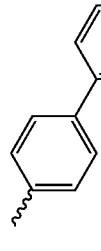 |

TABLE-continued
| 번호 | R1 | R2 | Ar1 | Ar2 |
|---|---|---|---|---|
| 7-9 | 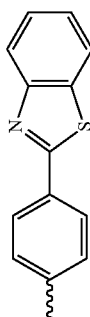 | 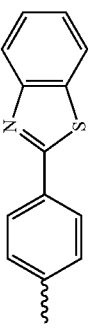 | 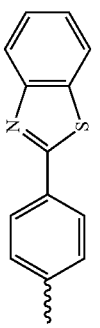 | 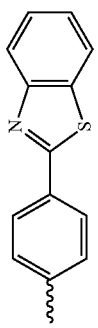 |
| 7-10 | 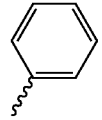 | 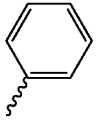 | 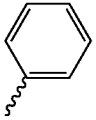 | 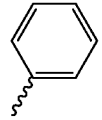 |
| 7-11 | 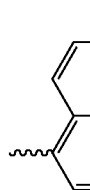 | 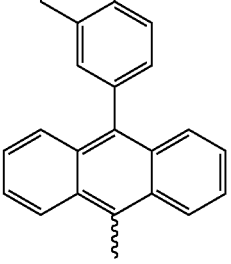 | 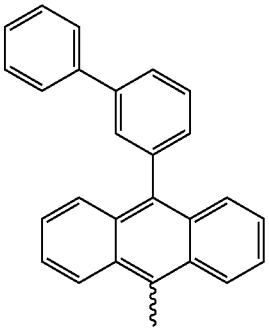 | 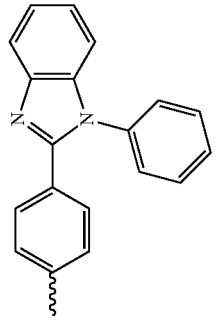 |
| 7-12 | 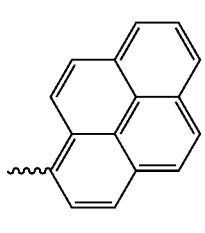 | 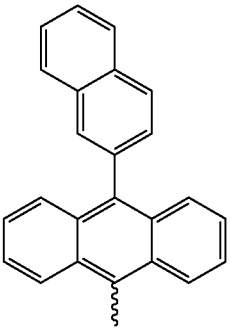 | 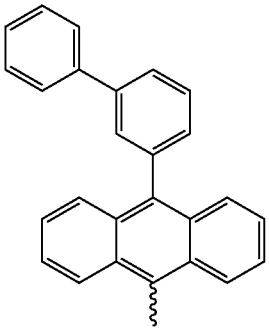 | 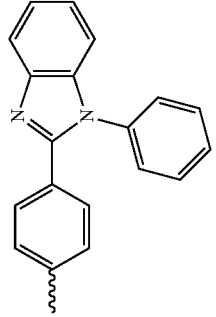 |

| 번호 | R1 | R2 | Ar1 | Ar2 |
|---|---|---|---|---|
| 7-13 | 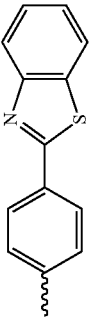 | 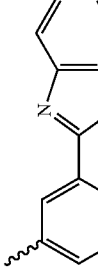 | 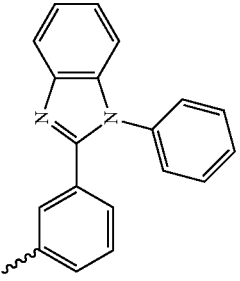 | 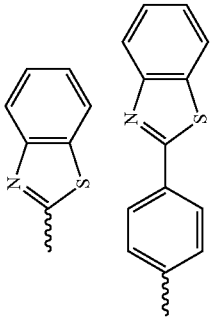 |
| 7-14 | 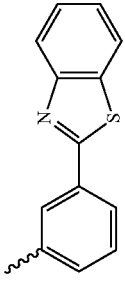 | 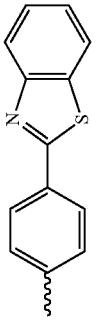 | 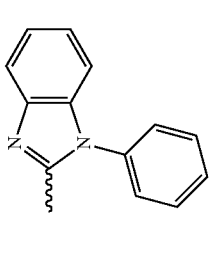 | 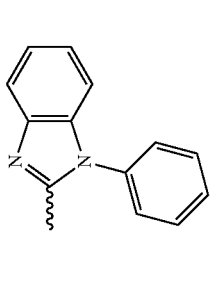 |
| 7-15 | 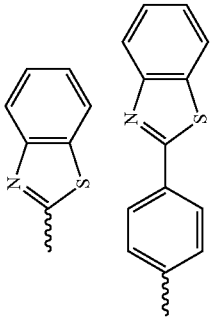 | 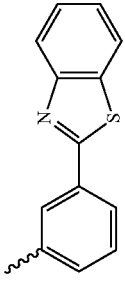 | 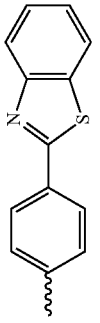 | 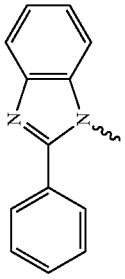 |
| 7-16 |  | 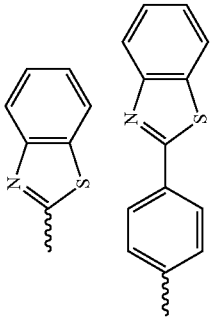 | 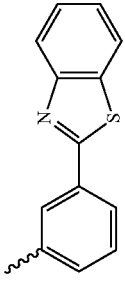 | 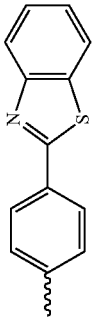 |
| 7-17 | 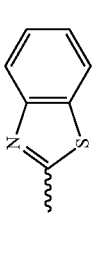 | 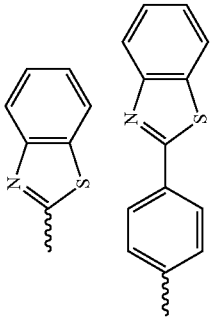 | 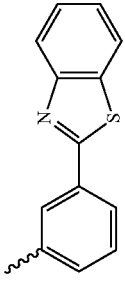 | 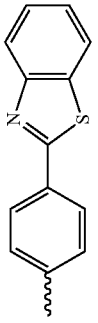 |
| 7-18 | 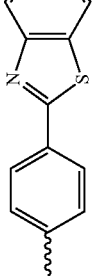 | 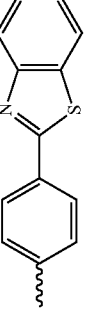 | 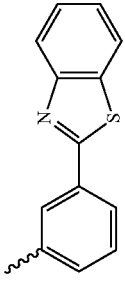 | 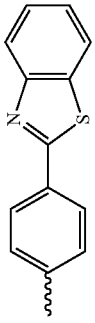 |

TABLE-continued
| 번호 | R1 | R2 | Ar1 | Ar2 |
|---|---|---|---|---|
| 7-19 | 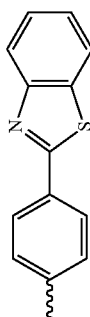 | 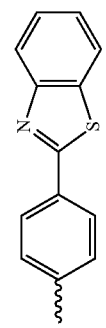 | 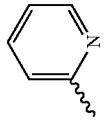 | 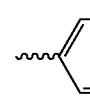 |
| 7-20 | 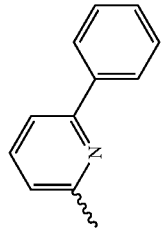 | 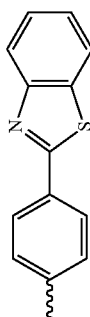 | 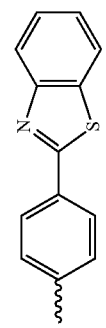 | 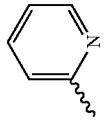 |
| 7-21 | 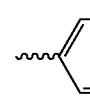 | 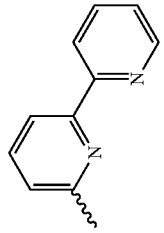 | 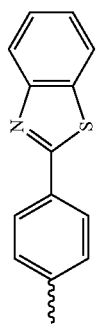 | 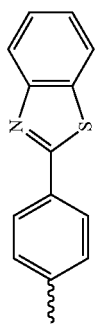 |
| 7-22 | 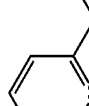 | 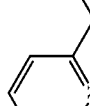 | 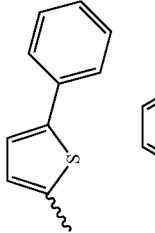 | 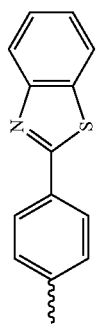 |
| 7-23 | 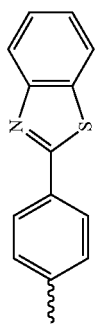 | 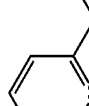 | 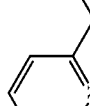 | 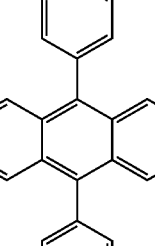 |
| 7-24 | 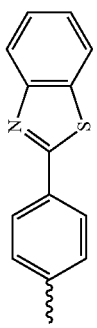 | 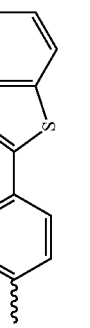 | 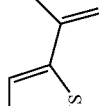 | 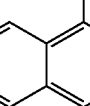 |

A method of preparing the fluorene derivative according to the present invention is described in detail in Preparation Examples as described below.

In addition, the present invention provides an organic electronic device which is provided with a first electrode, a second electrode, and one or more organic material layers that are disposed between the first electrode and the second electrode and include the compound of Formula 1.

The organic electronic device of the present invention may be manufactured by using a typical manufacturing method and material of an organic electronic device, except that one or more organic material layers are formed by using the above-mentioned compounds.

Hereinafter, an organic light emitting device will be described exemplarily.

In an embodiment of the present invention, the organic light emitting device may have a structure which includes a first electrode, a second electrode, and an organic material layer disposed between the first electrode and the second electrode. In the organic light emitting device according to the present invention, the organic material layer may have a single layer or a multilayer structure having two or more layers and including a light emitting layer. In the case of when the organic material layer of the organic light emitting device according to the present invention has the multilayer structure, the organic material layer may have a laminate structure including, for example, a hole injection layer, a hole transport layer, a light emitting layer, and an electron transport layer. However, the structure of the organic light emitting device is not limited thereto, but may have a smaller number of organic material layers. For example, the organic light emitting device according to the present invention may have the structure shown in FIG. 1, but is not limited thereto. In FIG. 1, reference numeral 1 denotes a substrate, reference numeral 2 denotes an anode, reference numeral 3 denotes a hole injection layer, reference numeral 4 denotes a hole transport layer, reference numeral 5 denotes an organic light emitting layer, reference numeral 6 denotes an electron transport layer, and reference numeral 7 denotes a cathode. The organic light emitting device which has the structure shown in FIG. 1 is called a forward direction type organic light emitting device. The scope of the present invention is not limited thereto, but includes a reverse direction type organic light emitting device. That is, the organic light emitting device according to the present invention may have a structure which includes the substrate, the cathode, the electron transport layer, the organic light emitting layer, the hole transport layer, the hole injection layer, and the anode sequentially layered.

For example, if the organic light emitting device according to the present invention includes the organic material layer having the multilayer structure, the compound of Formula 1 may be contained in a light emitting layer, a hole injection layer, a hole transport layer, a layer which transports holes and emits light simultaneously, a layer which emits light and transports electrons simultaneously, an electron transport layer, an electron transport and/or injection layer. In the present invention, it is more preferable that the compound of Formula 1 be contained in the electron injection and/or electron transport layer or the light emitting layer.

The organic light emitting device according to the present invention may be manufactured by using a typical manufacturing method and material of an organic light emitting device, except that the above-mentioned compound of Formula 1 is applied to one or more organic material layers of the organic light emitting device. For example, in order to manufacture the organic light emitting device according to the present invention, metal, conductive metal oxide or an alloy thereof may be deposited on a substrate by using a PVD (physical vapor deposition) method such as sputtering or e-beam evaporation, so as to form an anode. And the organic material layer which includes the hole injection layer, the hole transport layer, the light emitting layer, and the electron transport layer may be formed on the anode, and a substance which is capable of being used as the cathode may be deposited thereon. Unlike the above-mentioned method, in order to manufacture the organic light emitting device having the reverse direction structure, a cathode substance, an organic material layer, and an anode substance may be sequentially deposited on the substrate.

The organic material layer may be produced by means of various types of polymer materials by using not a deposit ion method but a solvent process such as spin coating, dip coating, doctor blading, screen printing, inkjet printing, heat transfer method or the like, so that the organic material layer has a small number of layers.

It is preferable that the anode material have a large work function so that a hole is desirably injected into the organic material layer. Specific examples of the anode material which is capable of being used in the present invention include, but are not limited to, metal such as vanadium, chrome, copper, zinc, and gold, or an alloy thereof; metal oxides such as zinc oxides, indium oxides, indium tin oxides (ITO), and indium zinc oxides (IZO); a combination of metal and oxides such as $ZnO:Al$ and $SnO_2:Sb$; and conductive polymers such as poly (3-methylthiophene), poly[3,4-(ethylene-1,2-dioxy) thiophene] (PEDT), polypyrrole, and polyaniline.

It is preferable that the cathode material have a small work function so that an electron is desirably injected into the organic material layer. Specific examples of the cathode material include, but are not limited to, metal such as magnesium, calcium, sodium, potassium, titanium, indium, yttrium, lithium, gadolinium, aluminum, silver, tin, and lead, or an alloy thereof; and a multilayered material such as LiF/Al and $LiO_2/Al$.

The hole injecting material is a material that is capable of desirably receiving a hole from an anode at low voltage. It is preferable that the HOMO (highest occupied molecular orbital) level of the hole injecting material be located between the work function of the anode material and the HOMO level of its neighboring organic material layer. Specific examples of the hole injecting material include, but are not limited to, organic materials of metal porphyrin, oligothiophene, and arylamine series, organic materials of hexanitrile hexaazatriphenylene and quinacridone series, organic materials of perylene series, and conductive polymers of on anthraquinone, polyaniline, and polythiophene series.

The hole transporting material is suitably a material having high hole mobility, which is capable of transferring holes from the anode or the hole injection layer toward the light emitting layer. Specific examples of the hole transporting material include, but are not limited to, organic materials of arylamine series, conductive polymers, and block copolymers having both conjugated portions and non-conjugated portions.

The light emitting material is a material capable of emitting visible light by accepting and recombining holes from the hole transport layer and electrons from the electron transport layer, and preferably a material having high quantum efficiency for fluorescence and phosphorescence. Specific examples of the light emitting material include, but are not limited to, 8-hydroxyquinoline aluminum complex ($Alq_3$); compounds of carbazole series; dimerized styryl compounds; BAlq; 10-hydroxybenzoquinoline-metal compounds; compounds of benzoxazole, benzthiazole, and benzimidazole series; polymers of poly(p-phenylenevinylene) (PPV) series; Spiro compounds; and compounds of polyfluorene and rubrene series.

The electron transport material is suitably a material having high electron mobility, which is capable of transferring electrons from the cathode to the light emitting layer. Specific examples of the electron transport material include, but are not limited to, 8-hydroxyquinoline aluminum complex; complexes including Alga; organic radical compounds; and hydroxyflavone-metal complexes.

The organic light emitting device according to the present invention may be a top light emitting type, a bottom light emitting type, or a dual-sided light emitting type according to the type of material used.

The compound according to the present invention may function in an organic electronic device such as an organic solar cell, an organic photoconducting (OPC) drum, and an organic transistor with a similar mechanism in the organic light emitting device.

MODE FOR INVENTION

A better understanding of the present invention may be obtained in light of the following Examples which are set forth to illustrate, but are not to be construed to limit the present invention.

Example

Preparation Example 1

Preparation of the Compound of Formula 1-A-1

4-bromobenzaldehyde diethyl acetal (7.0 g, 27 mmol) was diluted with 100 mL of anhydrous tetrahydrofuran and then maintained at −78° C. n-butyl lithium (2.5 M in Hex, 13.0 mL, 32.4 mmol) was dropped to the mixture and then agitated for 40 min. 2,7-dibromofluorene (7.6 g, 22.5 mmol) was added thereto. The react ion solution was agitated at −78° C. for 4 hours. After the reaction temperature was increased to normal temperature, 2N HCl aqueous solution was added to the reaction solution and then agitated for 6 hours. The layer was separated by using ethyl ether and dried with anhydrous magnesium. After the separated organic solvent layer was left at a reduced pressure, the compound of Formula 1-A-1 (5.2 g, yield 67%) was obtained by using a column purification method (SiO$_2$, EtOAc/Hexane=1/10).

MS:[M—H2O+H]$^+$=427

Preparation Example 2

Preparation of the Compound of Formula 1-B-1

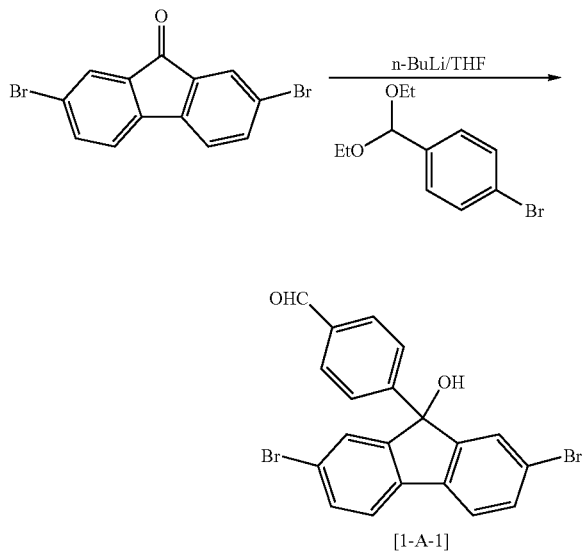

50 mL of toluene and 10 mL of acetic acid were added to the compound of Formula 1-A-1 (4.2 g, 9.5 mmol) and N-phenyl-1,2-diamino benzene (1.75 g, 9.5 mmol), and heated and agitated for 24 hours. The temperature was reduced to normal temperature, distilled water was added to form precipitates, and the filtration was then performed. After the separated organic solvent layer was left at a reduced pressure, the compound of Formula 1-B-1 (4.3 g, yield 74%) was obtained by using a column purification method (SiO$_2$, tetrahydrofuran:hexane=1:6).

MS:[M—H$_2$O+H]$^+$=591

Preparation Example 3

Preparation of the Compound of Formula 1-C-1

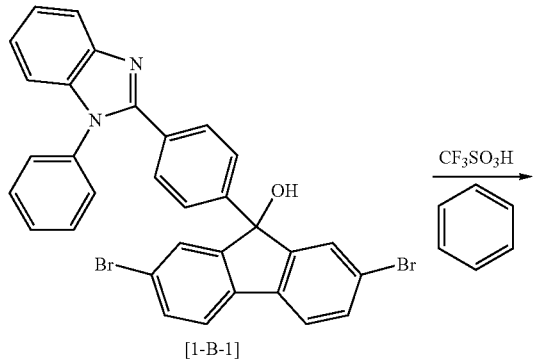

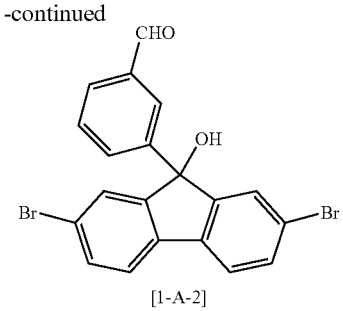

[1-A-2]

In the method of preparing the compound of Formula 1-A-1 of Preparation Example 1, the compound of Formula 1-A-2 was prepared by using the same method as Preparation Example 1, except that 3-bromobenzaldehyde diethyl acetal was used instead of 4-bromobenzaldehyde diethyl acetal.
MS:[M—H$_2$O]$^+$=427

Preparation Example 5

Preparation of the Compound of Formula 1-B-2

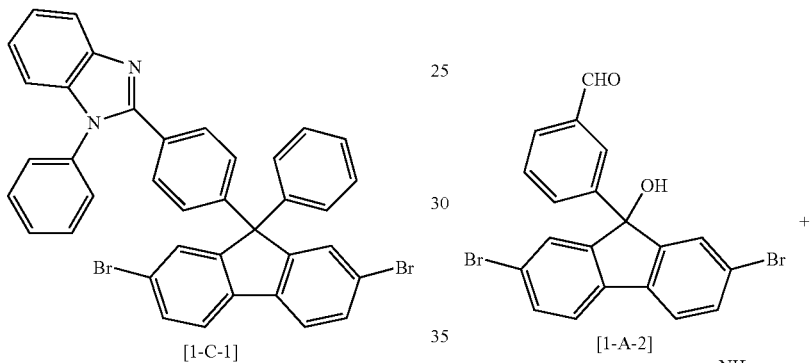

The compound of Formula 1-B-1 (4.3 g, 7.0 mmol) and benzene (50 mL) were mixed with each other, and CF$_3$SO$_3$H (1.6 mL, 18.4 mmol) were added thereto to perform the reflux at 80° C. for 6 hours. The cooling was performed to 0° C. by using the ice-bath, and the saturated NaHCO$_3$ aqueous solution was added to the reaction solution. After the layer separation was performed by using water and ethyl acetate, the organic layer was separated and dried with anhydrous magnesium. Subsequently, the organic layer was reduced in pressure, and the recrystallization was performed by using THF/hexane to prepare the compound of Formula 1-C-1 (2.5 g, yield 53%).
MS:[M+H]$^+$=669

Preparation Example 4

Preparation of the Compound of Formula 1-A-2

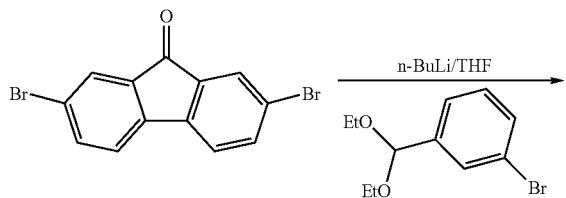

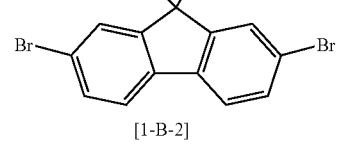

In the method of preparing the compound of Formula 1-B-1 of Preparation Example 2, the compound of Formula 1-B-2 was prepared by using the same method as the compound of Formula 1-B-1 of Preparation Example 2, except that the compound of Formula 1-A-2 was used instead of the compound of Formula 1-A-1.
MS:[M—H$_2$O]$^+$=591

Preparation Example 6

Preparation of the Compound of Formula 1-C-2

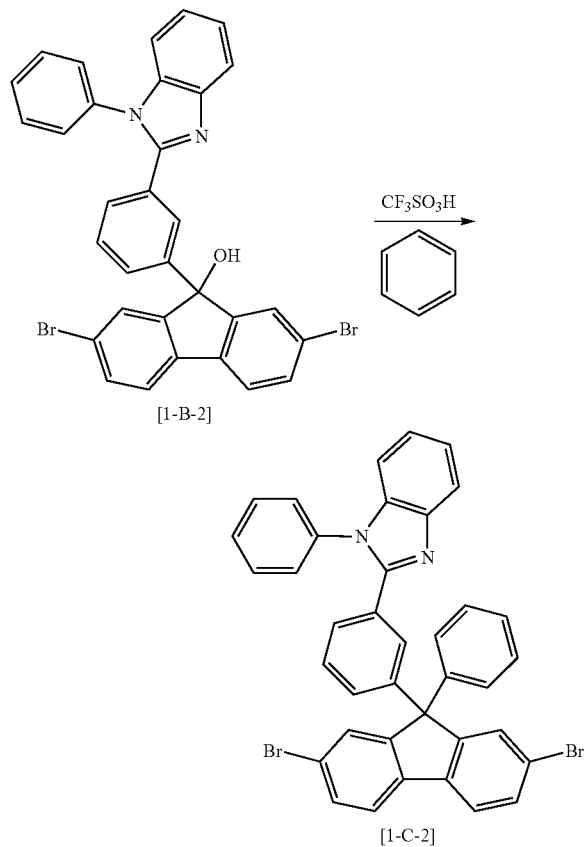

In the method of preparing the compound of Formula 1-C-1 of Preparation Example 3, the compound of Formula 1-C-2 was prepared by using the same method as the preparation method of Preparation Example 3, except that the compound of Formula 1-B-2 was used instead of the compound of Formula 1-B-1.

MS:[M+H]$^+$=669

Preparation Example 7

Preparation of the Compound of Formula 1-A-3

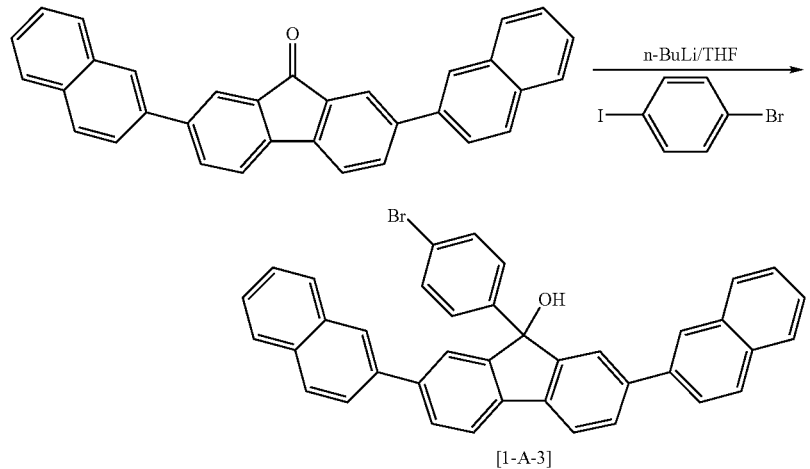

In the method of preparing the compound of Formula 1-A-1 of Preparation Example 1, the compound of Formula 1-A-3 was prepared by using the same method as the preparation method of Preparation Example 1, except that 1-bromo-4-iodobenzene was used instead of 4-bromobenzaldehyde diethyl acetal and 2,7-dinaphthylfluorene was used instead of 2,7-dibromofluorene.

MS:[M—H$_2$O]$^+$=572

Preparation Example 8

Preparation of the Compound of Formula 1-C-3

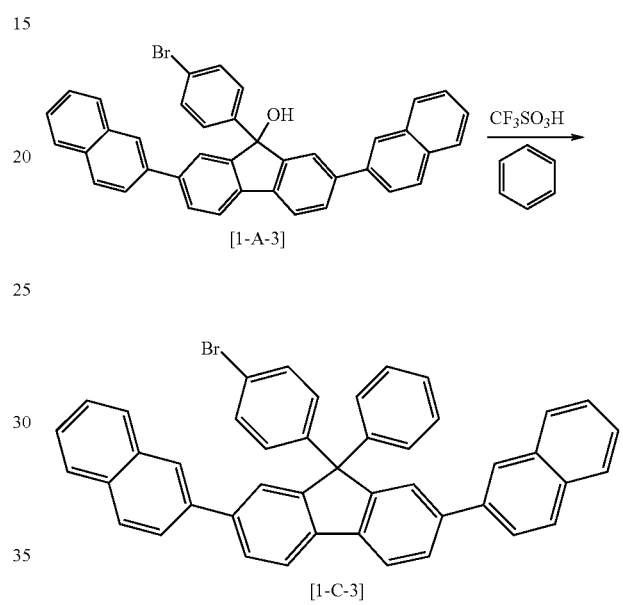

In the method of preparing the compound of Formula 1-C-1 of Preparation Example 3, the compound of Formula 1-C-3 was prepared by using the same method as the preparation method of Preparation Example 3, except that the compound of Formula 1-A-3 was used instead of the compound of Formula 1-B-1.

MS:[M]$^+$=649

Preparation Example 9

Preparation of the Compound of Formula 1-E-3

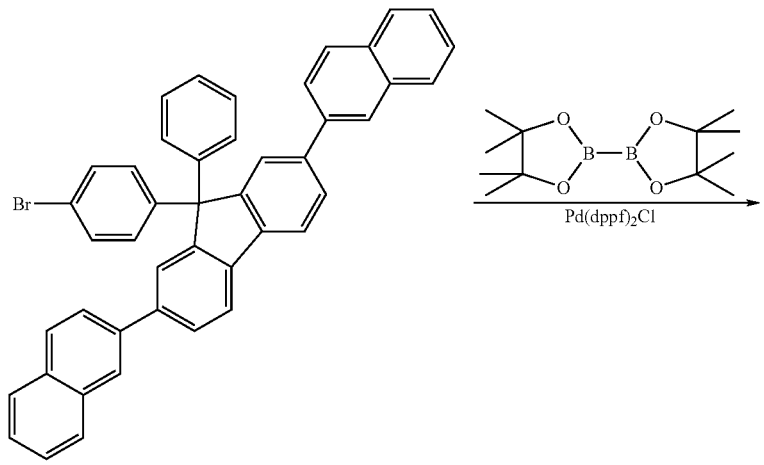

[1-C-3]

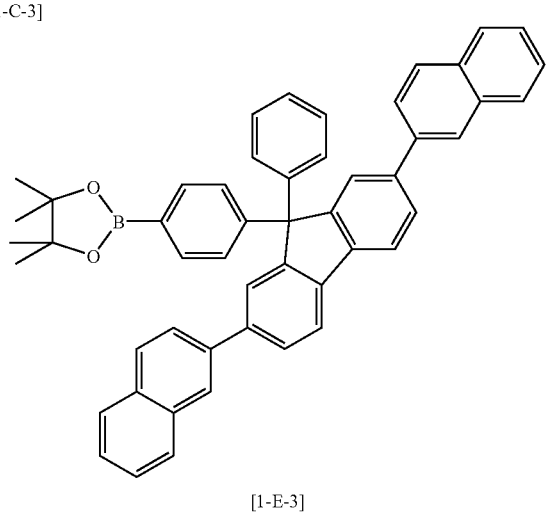

[1-E-3]

The compound of Formula 1-C-3 (16.9 g, 26 mmol) prepared in Preparation Example 8, bis(pinacolrato)diboron (7.8 g, 31 mmol), and potassium acetate (7.7 g, 78 mmol) were suspended in dioxane (200 mL). Palladium(diphenylphosphinoferrocene) chloride (0.6 g, 0.78 mmol) was added to the suspension solution. The mixture was agitated at 120° C. for about 6 hours, and then cooled to room temperature. The mixture was diluted with water (50 mL) and extracted with dichloromethane (3×50 mL). The organic extract material was dried by using magnesium sulfide and concentrated in a vacuum. The product was washed with ethanol and dried in a vacuum to prepare a compound of Formula 1-E-3 (11 g, yield 61%).

MS:[M+H]$^+$=697

Preparation Example 10

Preparation of the Compound of Formula 1-A-4

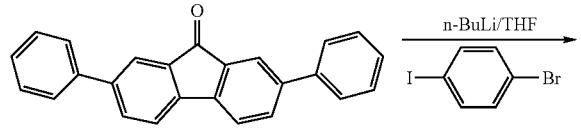

-continued

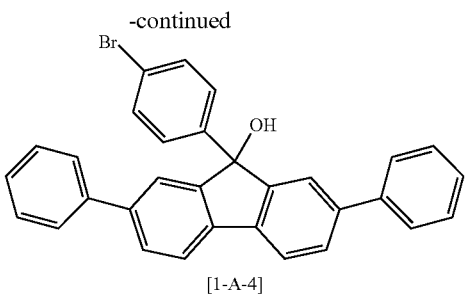

[1-A-4]

In the method of preparing the compound of Formula 1-A-1 of Preparation Example 1, the compound of Formula 1-A-4 was prepared by using the same method as the preparation method of Preparation Example 1, except that 1-bromo-4-iodobenzene was used instead of 4-bromobenzaldehyde diethyl acetal and 2,7-diphenyl fluorene was used instead of 2,7-dibromofluorene.

MS:[M—H$_2$O]$^+$=472

Preparation Example 11

Preparation of the Compound of Formula 1-C-4

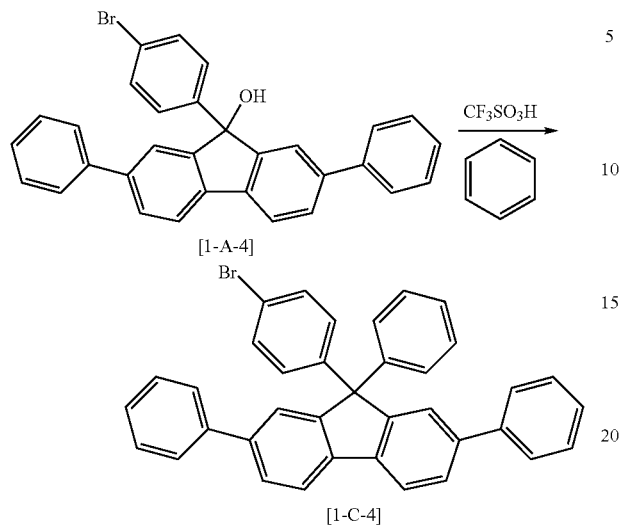

In the method of preparing the compound of Formula 1-C-1 of Preparation Example 3, the compound of Formula 1-C-4 was prepared by using the same method as the preparation method of Preparation Example 3, except that the compound of Formula 1-A-4 was used instead of the compound of Formula 1-B-1.

MS:[M]$^+$=549

Preparation Example 12

Preparation of the Compound of Formula 1-E-4

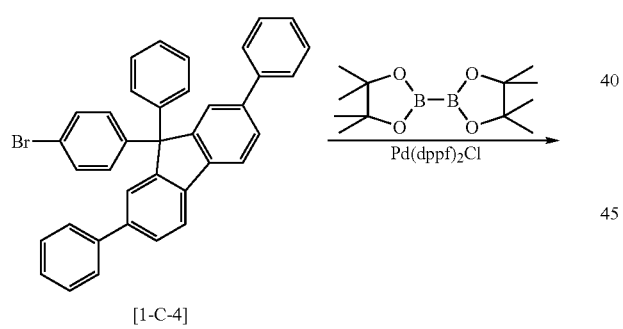

The compound of Formula 1-C-4 (42.9 g, 78 mmol) prepared in Preparation Example 10, bis(pinacolrato)diboron (23.4 g, 92 mmol), and potassium acetate (23 g, 234 mmol) were suspended in dioxane (400 mL). Palladium(diphenylphosphinoferrocene) chloride (1.7 g, 2.34 mmol) was added to the suspension solution. The mixture was agitated at 120° C. for about 6 hours, and then cooled to room temperature. The mixture was diluted with water (50 mL) and extracted with dichloromethane (3×50 mL). The organic extract material was dried by using magnesium sulfide and concentrated in a vacuum. The product was washed with ethanol and dried in a vacuum to prepare a compound of Formula 1-E-4 (32 g, yield 68.8%).

MS:[M+H]$^+$=597

Example 1

Synthesis of the Compound of Formula 1-5

[Formula 1-5]

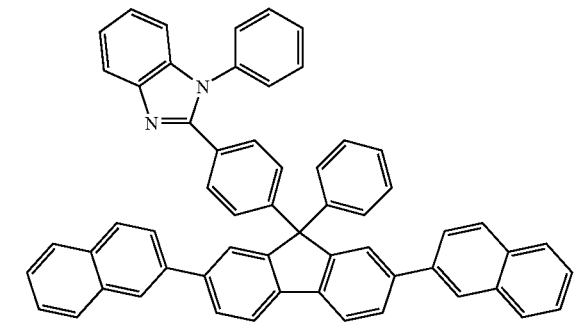

The compound of Formula 1-C-1 (2.5 g, 3.74 mmol), naphthyl-2-boronic acid (1.6 g, 9.4 mmol) were added to 30 mL of toluene, 10 mL of ethanol, and 20 mL of 2M potassium carbonate aqueous solution, tetrabistriphenylphosphino palladium (150 mg, 0.13 mmol) was added thereto, and heating and agitation were performed for 15 hours. The temperature was reduced to normal temperature, the water layer was removed, the drying was performed by using anhydrous magnesium sulfide, and the concentration was performed at a reduced pressure to perform recrystallization with petrol ether, thus preparing the compound of Formula 1-5 (2.6 g, yield 90%).

MS:[M+H]$^+$=763

UV (2×10$^{-5}$M toluene solution): $\lambda_{max}$ 335 nm

PL (2×10$^{-5}$M toluene solution): $\lambda_{max}$ 400 nm

Example 2

Synthesis of the Compound of Formula 1-8

[Formula 1-8]

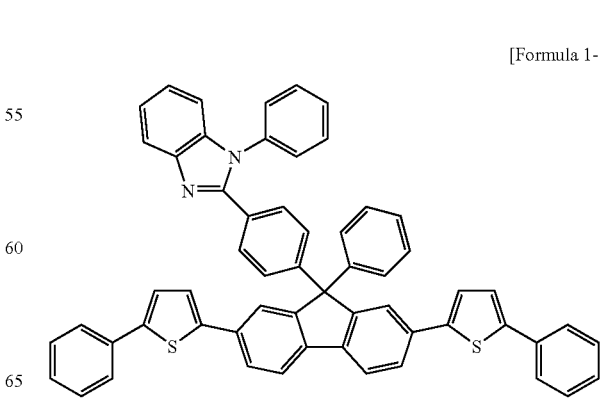

The compound of Formula 1-8 was prepared by using the same method as Example 1, except that the naphthyl-1-boronic acid was used instead of the naphthyl-2-boronic acid.

MS:[M+H]$^+$=763

UV (2×10$^{-5}$ M toluene solution): $\lambda_{max}$ 311 nm

PL (2×10$^{-5}$M toluene solution): $\lambda_{max}$ 399 nm

Example 3

Synthesis of the Compound of Formula 1-23

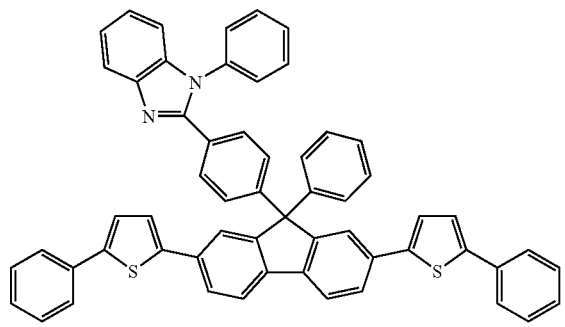

[Formula 1-23]

The compound of Formula 1-23 was prepared by using the same method as Example 1, except that the 5-phenylthiophenyl-2-boronic acid was used instead of the naphthyl-2-boronic acid.

MS:[M+H]$^+$=827

Example 4

Synthesis of the Compound of Formula 2-5

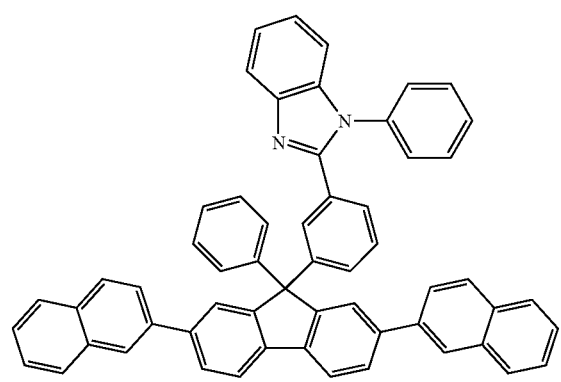

[Formula 2-5]

The compound of Formula 2-5 was prepared by using the same method as Example 1, except that the compound of Formula 1-C-2 was used instead of the compound of Formula 1-C-1.

MS:[M+H]$^+$=763

Example 5

Synthesis of the Compound of Formula 3-5

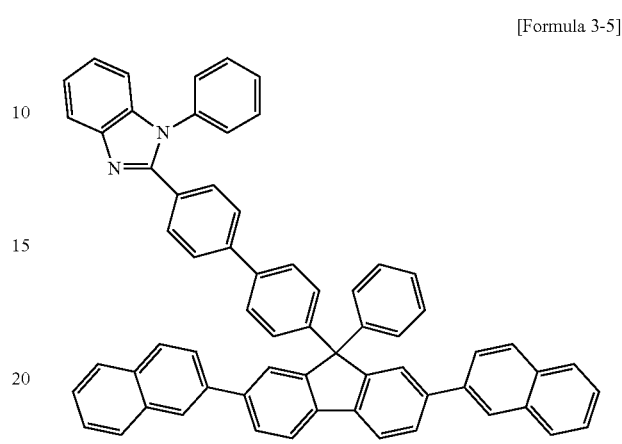

[Formula 3-5]

The compound of Formula 3-5 was prepared by using the same method as Example 1, except that the compound of Formula 1-C-3 was used instead of the compound of Formula 1-C-1.

MS:[M+H]$^+$=839

Example 6

Synthesis of the Compound of Formula 6-2

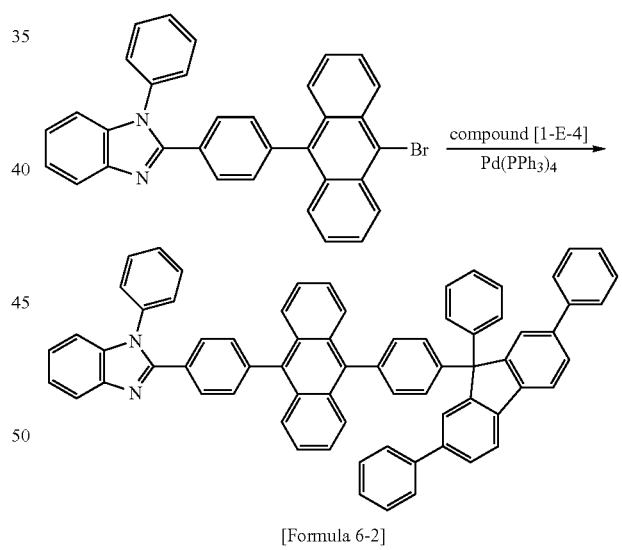

[Formula 6-2]

The bromo compound (2.7 g, 5 mmol), the compound of Formula 1-E-4 (3.0 g, 5 mmol), and sodium carbonate (1.4 g, 10 mmol) were suspended in the mixture of tetrahydrofuran (100 mL) and water (50 mL). Tetrakis(triphenylphosphine) palladium [II] (0.46 g, 0.4 mmol) was added to the suspension solution. The mixture was agitated in a ref lux for about 24 hours, and then cooled to room temperature. The organic layer was separated, and the aqueous layer was extracted with tetrahydrofuran. The combined organic extracts were dried by using magnesium sulfide and concentrated in a vacuum. The purification was performed by using THF/EtOH to prepare the compound of Formula 6-2 (3.2 g, yield 69%).

MS:[M+H]$^+$=915

Example 7

Synthesis of the Compound of Formula 4-2

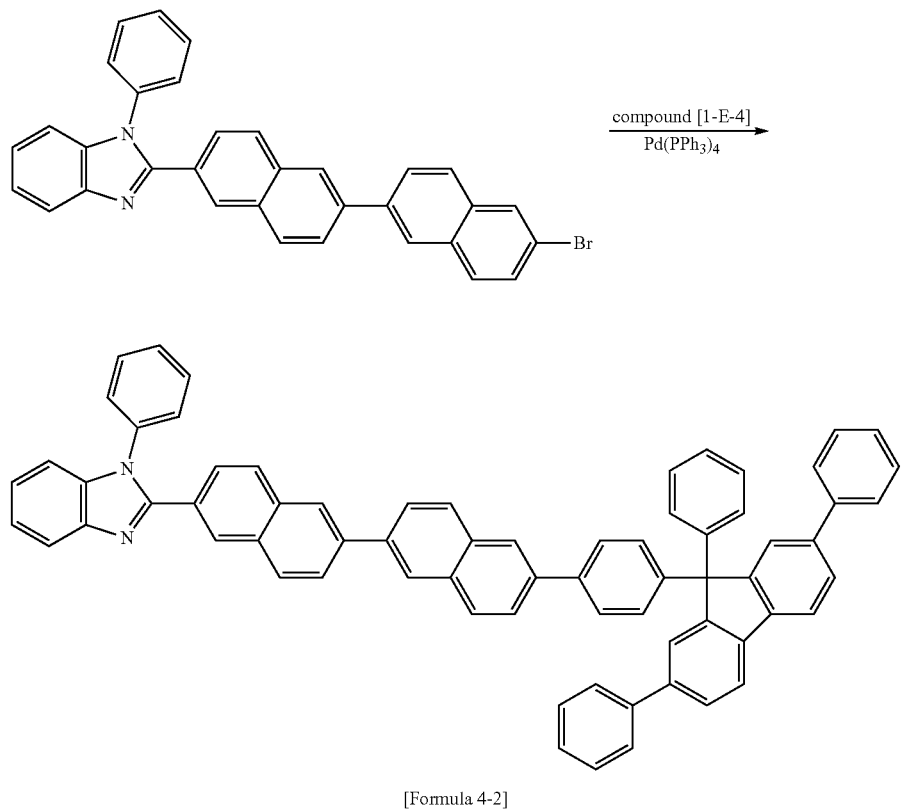

[Formula 4-2]

The bromo compound (5.3 g, 10 mmol), the compound of Formula 1-E-4 (6.0 g, 10 mmol), and sodium carbonate (2.8 g, 20 mmol) were suspended in the mixture of tetrahydrofuran (200 mL) and water (50 mL). Tetrakis(triphenylphosphine)palladium [II] (0.46 g, 0.4 mmol) was added to the suspension solution. The mixture was agitated in a reflux for about 24 hours, and then cooled to room temperature. The organic layer was separated, and the aqueous layer was extracted with tetrahydrofuran. The combined organic extracts were dried by using magnesium sulfide and concentrated in a vacuum. The purification was performed by using THF/EtOH to prepare the compound of Formula 4-2 (7.1 g, yield 78%).

MS:$[M+H]^+$=915

Experimental Example 1

The glass substrate that was thinly coated with ITO (indium tin oxide) to a thickness of 1500 Å was immersed in distilled water in which a detergent was dissolved and washed with a ultrasonic wave. In connection with this, the detergent was products manufactured by Fischer Co., and distil led water was filtered twice by using a filter manufactured by Millipore Co. After ITO was washed for 30 min, the ultrasonic wave washing was repeated twice by using distilled water for 10 min. After the washing with distilled water was finished, the ultrasonic wave washing was performed by using a solvent such as isopropyl alcohol, acetone, or methanol, and the washed glass substrate was dried, and transported to a plasma washing machine. Additionally, the substrate was washed by using an oxygen plasma for 5 min and then transported to a vacuum deposition machine.

Hexanitrile hexaazatriphenylene (HAT) of the following formula was deposited on the prepared ITO transparent electrode in a vacuum by heating to a thickness of 500 Å to form the hole injection layer.

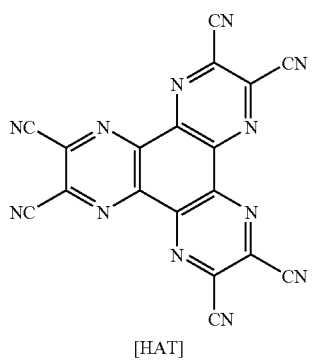

[HAT]

The substance that was used to transport a hole such as 4,4'-bis[N-(1-naphthyl)-N-phenylamino]biphenyl (NPB) (400 Å) of the following Formula was deposited on the hole injection layer in a vacuum to form a hole transport layer.

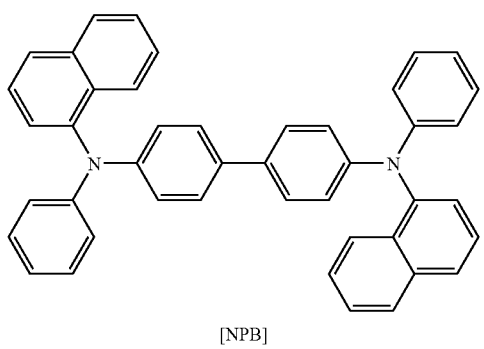

[NPB]

Subsequently, Alq₃ (aluminum tris(8-hydroxyquinoline)) of the following Formula was deposited on the hole transport layer in a vacuum to a thickness of 300 Å to form a light emitting layer.

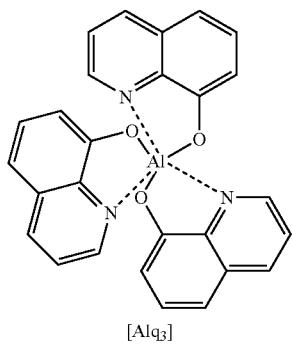

[Alq₃]

The compound of Formula 1-5 prepared in Example 1 was deposited on the light emitting layer in a vacuum to a thickness of 200 Å to form an electron injection layer and an electron transport layer.

Lithium fluoride (LiF) and aluminum were sequentially deposited on the electron injection layer and the electron transport layer to a thickness of 12 Å and 2000 Å to form a cathode.

In this connection, the deposition rate of the organic substance was maintained at 0.4 to 0.7 Å/sec, the deposition rate of lithium fluoride of the cathode was maintained at 0.3 Å/sec, the deposition rate of aluminum was maintained at 2 Å/sec, and the degree of vacuum was maintained at $2 \times 10^{-7}$ to $5 \times 10^{-8}$ torr during the deposition.

In the case of when a forward electric field of 7.1 V was applied to the manufactured organic light emitting device to emit light, the intensity of 10.31 cd/A was obtained at a current density of 100 mA/cm², and green light corresponding to x of 0.33 and y of 0.52 was observed based on the 1931 CIE color coordinate.

Experimental Example 2

Hexanitrile hexaazatriphenylene (500 Å), 4,4'-bis[N-(1-naphthyl)-N-phenylamino]biphenyl (NPB) (400 Å), Alq₃ (300 Å), and the compound of Formula 1-8 (200 Å) prepared in Example 2 were sequentially deposited on the ITO electrode which was prepared by using the same method as Experimental Example 1 in a vacuum by heating, so as to sequentially form the hole injection layer, the hole transport layer, the light emitting layer, and the electron transport layer.

Lithium fluoride (LiF) and aluminum were sequentially deposited on the electron transport layer to a thickness of 12 Å and 2000 Å to form a cathode. Thereby, an organic light emitting device was manufactured.

In this connection, the deposition rate of the organic substance was maintained at 0.4 to 0.7 Å/sec, the deposition rate of lithium fluoride of the cathode was maintained at 0.3 Å/sec, the deposition rate of aluminum was maintained at 2 Å/sec, and the degree of vacuum was maintained at $2 \times 10^{-7}$ to $5 \times 10^{-8}$ torr during the deposition.

In the case of when a forward electric field of 7.6 V was applied to the manufactured organic light emitting device, the intensity of 7.99 cd/A was obtained at a current density of 100 mA/cm², and green light corresponding to x of 0.33 and y of 0.50 was observed based on the 1931 CIE color coordinate.

The invention claimed is:
1. A fluorene derivative represented by Formula 1:

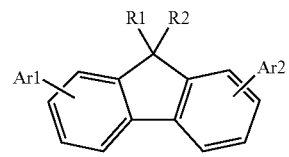

[Formula 1]

wherein R1 is a group of Formula 2:

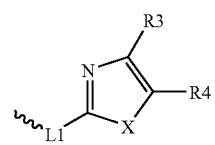

[Formula 2]

R2 is a group of Formula 3:

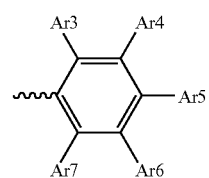

[Formula 3]

wherein R3 and R4 are each independently a $C_6$ to $C_{30}$ aryl group which is substituted or unsubstituted by one or more groups selected from the group consisting of a $C_6$ to $C_{30}$ aryl group and a $C_5$ to $C_{30}$ heteroaryl group; or a $C_5$ to $C_{30}$ aliphatic heterocyclic group or a aromatic heterocyclic group which is substituted or unsubstituted by one or more groups selected from the group consisting of a $C_6$ to $C_{30}$ aryl group and a $C_5$ to $C_{30}$ heteroaryl group, and are bonded to each other to form a condensation ring group of an aryl group, a heteroaryl group, or an aliphatic group, X is —N—Ar11, an oxygen atom, or a sulfur atom, and Ar11 is a $C_1$ to $C_{30}$ alkyl group, a $C_6$ to $C_{30}$ aryl group, or a $C_5$ to $C_{30}$ heteroaryl group, L1 is a direct bond, or selected from the group consisting of a $C_6$ to $C_{30}$ arylene group and a $C_5$ to $C_{30}$ heteroarylene group, and Ar1, Ar2, Ar3, Ar4, Ar5, Ar6 and Ar7 are the same or different, are each independently hydrogen; halogen; an amino group; a nitrile group; a nitro group; a $C_1$ to $C_{30}$ alkyl group; a $C_2$ to $C_{40}$ alkenyl group; a $C_6$ to $C_{30}$ aryl group which is substituted or unsubstituted by one or more groups selected from the group consisting of halogen, an amino group, a nitrile group, a nitro group, a $C_1$ to $C_{30}$ alkyl group, a $C_2$ to $C_{40}$ alkenyl group, a $C_1$ to $C_{40}$ alkoxy group, a $C_3$ to $C_{30}$ cycloalkyl group, a $C_3$ to $C_{30}$ heterocycloalkyl group, a $C_6$ to $C_{30}$ aryl group, and a $C_5$ to $C_{30}$ heteroaryl group; a $C_5$ to $C_{30}$ heterocyclic group which is substituted or unsubstituted by one or more groups selected from the group consisting of halogen, an amino group, a nitrile group, a nitro group, a $C_1$ to $C_{30}$ alkyl group, a $C_2$ to $C_{40}$ alkenyl group, a $C_1$ to $C_{40}$ alkoxy group, a $C_3$ to $C_{30}$ cycloalkyl group, a $C_3$ to $C_{30}$ heterocycloalkyl group, a $C_6$ to $C_{30}$ aryl group, and a $C_5$ to $C_{30}$ heteroaryl group; a $C_6$ to $C_{30}$ arylamino group which is substituted or unsubstituted by one or more groups selected from the group consisting of halogen, an amino group, a nitrile group, a nitro group, a $C_1$ to $C_{30}$ alkyl group, a $C_2$ to $C_{40}$ alkenyl group, a $C_1$ to $C_{40}$ alkoxy group, a $C_3$ to $C_{30}$ cycloalkyl group, a $C_3$ to $C_{30}$ heterocycloalkyl group, a $C_6$ to $C_{30}$ aryl group, and a $C_5$ to $C_{30}$ heteroaryl group; or a $C_5$ to $C_{30}$ heteroarylamino group which is substituted or unsubstituted by one or more groups selected from the group consisting of halogen, an amino group, a nitrile group, a nitro group, a $C_1$ to $C_{30}$ alkyl group, a $C_2$ to $C_{40}$ alkenyl group, a $C_1$ to $C_{40}$ alkoxy group, a $C_3$ to $C_{30}$ cycloalkyl group, a $C_3$ to $C_{30}$ heterocycloalkyl group, a $C_6$ to $C_{30}$ aryl group, and a $C_5$ to $C_{30}$ heteroaryl group.

2. The fluorene derivative as set forth in claim 1, wherein Ar1 and Ar2 are each independently selected from the group consisting of hydrogen; an aryl group selected from the group consisting of a phenyl group, a naphthyl group, a binaphthyl group, an anthracenyl group, a biphenyl group, a pyrenyl group, and a perylenyl group; and a heteroaryl group selected from the group consisting of a pyridyl group, a bipyridyl group, a triazinyl group, a thienyl group, an imidazolyl group, an oxazolyl group, a thiazolyl group, a triazolyl group, a quinolyl group, and an isoquinolyl group.

3. The fluorene derivative as set forth in claim 1, wherein Ar3, Ar4, Ar5, Ar6, and Ar7 are each independently selected from the group consisting of hydrogen; a methyl group; an ethyl group; and an aryl group selected from the group consisting of a phenyl group, a naphthyl group, an anthracenyl group, a biphenyl group, a pyrenyl group, and a perylenyl group.

4. The fluorene derivative as set forth in claim 1, wherein the compound of Formula 1 is selected from compounds of the following structural formulae:

TABLE

| Number | R1 | R2 | Ar1 | Ar2 |
|---|---|---|---|---|
| 1-1 | benzimidazole with phenyl (N-substituent) and p-phenyl (C2-substituent) | phenyl | H | H |
| 1-2 | benzimidazole with phenyl (N-substituent) and p-phenyl (C2-substituent) | phenyl | phenyl | phenyl |
| 1-3 | benzimidazole with phenyl (N-substituent) and p-phenyl (C2-substituent) | phenyl | biphenyl-4-yl | biphenyl-4-yl |
| 1-4 | benzimidazole with phenyl (N-substituent) and p-phenyl (C2-substituent) | phenyl | 3-(naphthalen-2-yl)phenyl | 3-(naphthalen-2-yl)phenyl |

TABLE-continued

| Number | R1 | R2 | Ar1 | Ar2 |
|---|---|---|---|---|
| 1-5 | 2-phenyl-1-phenyl-benzimidazolyl | phenyl | 2-naphthyl | 2-naphthyl |
| 1-6 | 2-phenyl-1-phenyl-benzimidazolyl | phenyl | 6-phenyl-2-naphthyl | 6-phenyl-2-naphthyl |
| 1-7 | 2-phenyl-1-phenyl-benzimidazolyl | phenyl | 6-(3-pyridyl)-2-naphthyl | 6-(3-pyridyl)-2-naphthyl |
| 1-8 | 2-phenyl-1-phenyl-benzimidazolyl | phenyl | 1-naphthyl | 1-naphthyl |
| 1-9 | 2-phenyl-1-phenyl-benzimidazolyl | phenyl | 1-pyrenyl | 1-pyrenyl |

TABLE-continued
| Number | R1 | R2 | Ar1 | Ar2 |
|---|---|---|---|---|
| 1-10 | 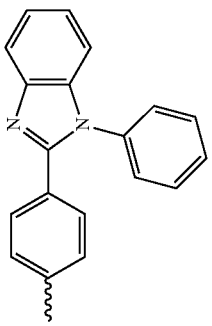 | 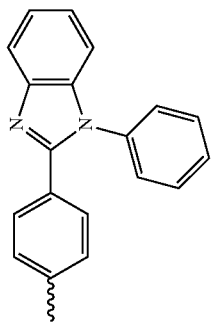 | 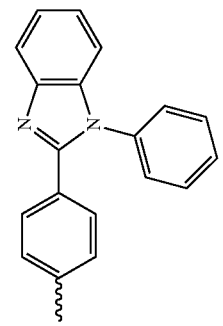 | 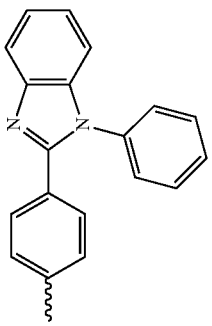 |
| 1-11 | 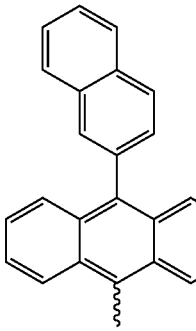 | 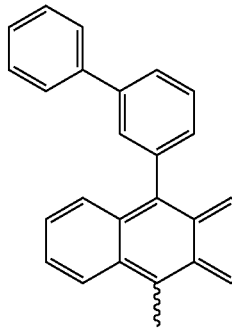 | 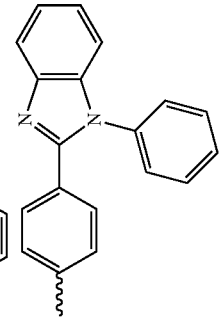 | 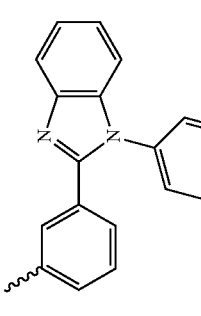 |
| 1-12 | 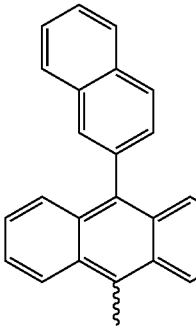 | 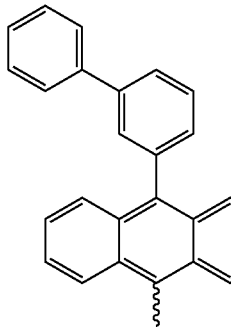 | 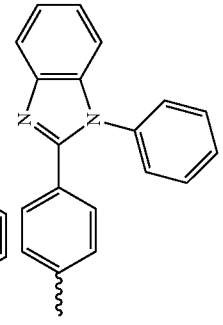 | 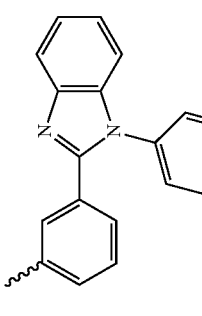 |
| 1-13 | 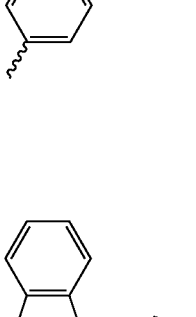 | 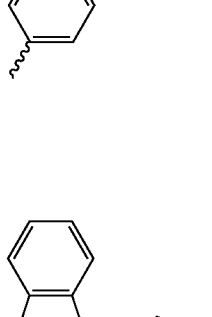 | 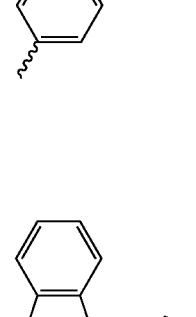 |  |

TABLE-continued
| Number | R1 | R2 | Ar1 | Ar2 |
|---|---|---|---|---|
| 1-14 | 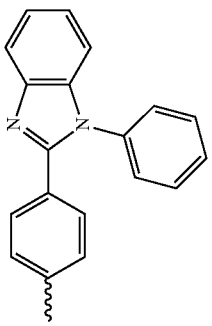 | 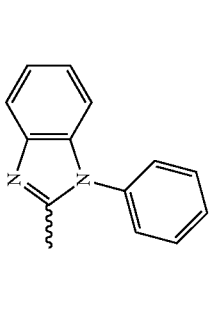 | 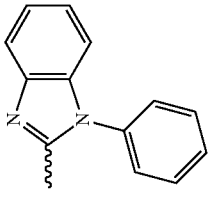 | 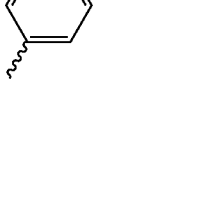 |
| 1-15 | 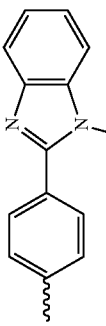 | 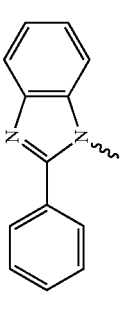 | 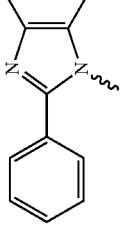 |  |
| 1-16 | 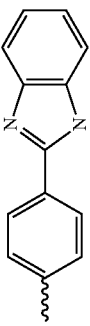 | 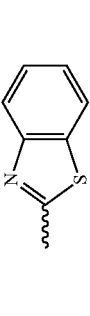 | 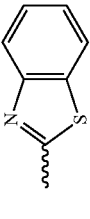 |  |
| 1-17 | 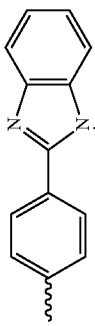 | 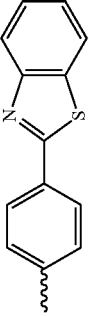 | 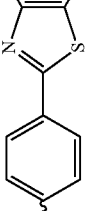 |  |
| 1-18 | 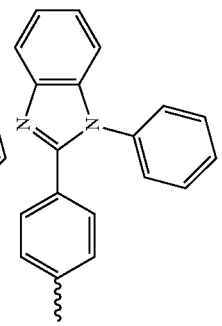 | 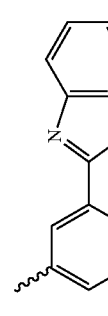 | 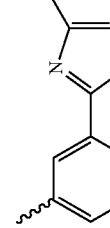 |  |

TABLE-continued
| Number | R1 | R2 | Ar1 | Ar2 |
|---|---|---|---|---|
| 1-19 | 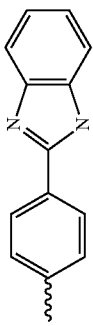 | 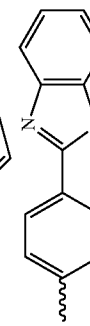 | 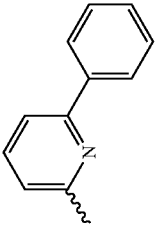 | 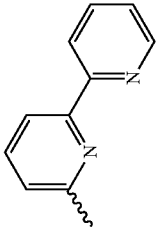 |
| 1-20 | 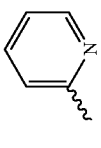 | 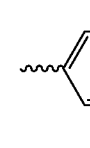 | 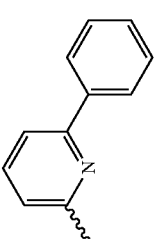 | 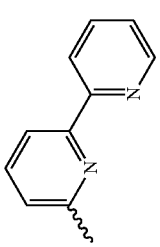 |
| 1-21 | 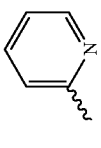 | 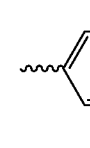 | 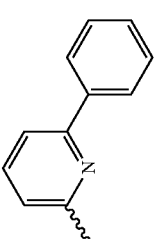 | 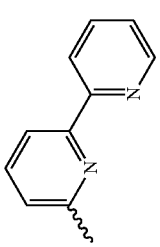 |
| 1-22 | 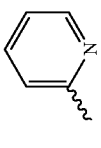 | 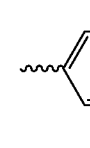 | 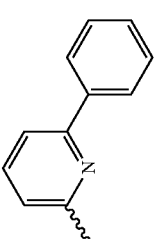 | 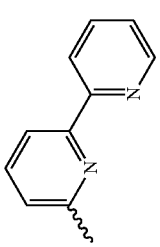 |
| 1-23 | 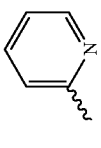 | 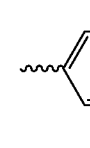 | 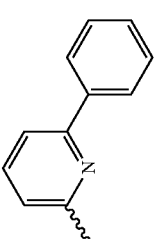 | 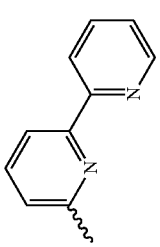 |

TABLE-continued

| Number | R1 | R2 | Ar1 | Ar2 |
|---|---|---|---|---|
| 1-24 | [2-phenyl-1-phenyl-benzimidazole, para-linked] | [phenyl] | [9-(2-naphthyl)-10-phenyl-anthracene] | |
| 2-1 | [2-phenyl-1-phenyl-benzimidazole, meta-linked] | [phenyl] | H | H |
| 2-2 | [2-phenyl-1-phenyl-benzimidazole, meta-linked] | [phenyl] | [phenyl] | [phenyl] |
| 2-3 | [2-phenyl-1-phenyl-benzimidazole, meta-linked] | [phenyl] | [biphenyl] | [biphenyl] |

TABLE-continued

| Number | R1 | R2 | Ar1 | Ar2 |
|---|---|---|---|---|
| 2-4 | | | | |
| 2-5 | | | | |
| 2-6 | | | | |
| 2-7 | | | | |

TABLE-continued

| Number | R1 | R2 | Ar1 | Ar2 |
|---|---|---|---|---|
| 2-8 | 2-phenyl-1-phenyl-benzimidazole (meta-linked phenyl) | phenyl | 1-naphthyl | 1-naphthyl |
| 2-9 | 2-phenyl-1-phenyl-benzimidazole (meta-linked phenyl) | phenyl | 1-pyrenyl | 1-pyrenyl |
| 2-10 | 2-phenyl-1-phenyl-benzimidazole (meta-linked phenyl) | phenyl | 10-(2-naphthyl)anthracen-9-yl | 10-(2-naphthyl)anthracen-9-yl |
| 2-11 | 2-phenyl-1-phenyl-benzimidazole (meta-linked phenyl) | phenyl | 10-(biphenyl-3-yl)anthracen-9-yl | 10-(biphenyl-3-yl)anthracen-9-yl |

TABLE-continued

| Number | R1 | R2 | Ar1 | Ar2 |
|---|---|---|---|---|
| 2-12 | | | | |
| 2-13 | | | | |
| 2-14 | | | | |
| 2-15 | | | | |

TABLE-continued

| Number | R1 | R2 | Ar1 | Ar2 |
|---|---|---|---|---|
| 2-16 | 2-phenyl-1-phenyl-benzimidazol-3-yl (meta) | phenyl | benzothiazol-2-yl | benzothiazol-2-yl |
| 2-17 | 2-phenyl-1-phenyl-benzimidazol-3-yl (meta) | phenyl | 2-(4-phenyl)benzothiazole | 2-(4-phenyl)benzothiazole |
| 2-18 | 2-phenyl-1-phenyl-benzimidazol-3-yl (meta) | phenyl | 2-(3-phenyl)benzothiazole | 2-(3-phenyl)benzothiazole |
| 2-19 | 2-phenyl-1-phenyl-benzimidazol-3-yl (meta) | phenyl | pyridin-2-yl | pyridin-2-yl |

TABLE-continued

| Number | R1 | R2 | Ar1 | Ar2 |
|---|---|---|---|---|
| 2-20 | | | | |
| 2-21 | | | | |
| 2-22 | | | | |
| 2-23 | | | | |

TABLE-continued

| Number | R1 | R2 | Ar1 | Ar2 |
|---|---|---|---|---|
| 2-24 | benzimidazole-phenyl | phenyl | 10-(2-naphthyl)anthracen-9-yl-phenyl | 10-(2-naphthyl)anthracen-9-yl-phenyl |
| 3-1 | benzimidazole-biphenyl | phenyl | H | H |
| 3-13 | benzimidazole-biphenyl | phenyl | benzimidazole-phenyl | benzimidazole-phenyl |
| 3-14 | benzimidazole-biphenyl | phenyl | benzimidazole-biphenyl | benzimidazole-biphenyl |

TABLE-continued

| Number | R1 | R2 | Ar1 | Ar2 |
|---|---|---|---|---|
| 3-15 | biphenyl-N-phenylbenzimidazol-2-yl | phenyl | 2-phenylbenzimidazol-1-yl | 2-phenylbenzimidazol-1-yl |
| 3-16 | biphenyl-N-phenylbenzimidazol-2-yl | phenyl | benzothiazol-2-yl | benzothiazol-2-yl |
| 3-17 | biphenyl-N-phenylbenzimidazol-2-yl | phenyl | 2-(4-phenyl)benzothiazol-2-yl | 2-(4-phenyl)benzothiazol-2-yl |
| 3-18 | biphenyl-N-phenylbenzimidazol-2-yl | phenyl | 2-(3-phenyl)benzothiazol-2-yl | 2-(3-phenyl)benzothiazol-2-yl |
| 3-19 | biphenyl-N-phenylbenzimidazol-2-yl | phenyl | pyridin-2-yl | pyridin-2-yl |

TABLE-continued

| Number | R1 | R2 | Ar1 | Ar2 |
|---|---|---|---|---|
| 3-20 | | | | |
| 3-21 | | | | |
| 3-22 | | | | |
| 3-23 | | | | |
| 3-24 | | | | |

TABLE-continued
| Number | R1 | R2 | Ar1 | Ar2 |
|---|---|---|---|---|
| 4-1 | 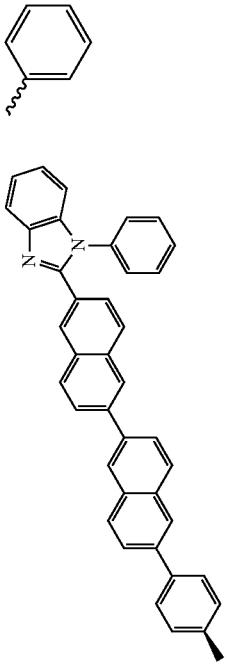 | 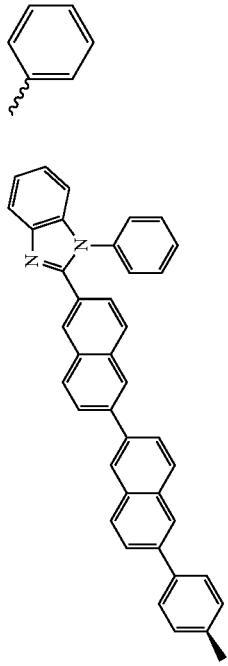 | H | H |
| 4-2 | 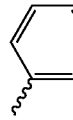 |  |  | 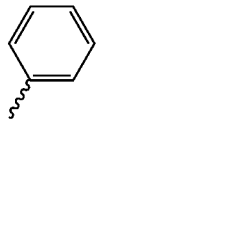 |
| 4-3 | 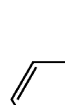 | 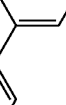 |  |  |
| 4-4 |  |  |  |  |

TABLE-continued

| Number | R1 | R2 | Ar1 | Ar2 |
|---|---|---|---|---|
| 4-5 | | | | |
| 4-6 | | | | |
| 4-7 | | | | |
| 4-8 | | | | |

TABLE-continued

| Number | R1 | R2 | Ar1 | Ar2 |
|---|---|---|---|---|
| 4-9 | | | | |
| 4-10 | | | | |
| 4-11 | | | | |
| 4-12 | | | | |

TABLE-continued

| Number | R1 | R2 | Ar1 | Ar2 |
|---|---|---|---|---|
| 4-13 | | | | |
| 4-14 | | | | |
| 4-15 | | | | |
| 4-16 | | | | |

TABLE-continued

| Number | R1 | R2 | Ar1 | Ar2 |
|---|---|---|---|---|
| 4-17 | naphthalene-naphthalene-phenyl substituted with 1-phenyl-benzimidazol-2-yl | phenyl | 2-(4-phenyl)benzothiazole | 2-(4-phenyl)benzothiazole |
| 4-18 | naphthalene-naphthalene-phenyl substituted with 1-phenyl-benzimidazol-2-yl | phenyl | 2-(3-phenyl)benzothiazole | 2-(3-phenyl)benzothiazole |
| 4-19 | naphthalene-naphthalene-phenyl substituted with 1-phenyl-benzimidazol-2-yl | phenyl | 2-pyridyl | 2-pyridyl |
| 4-20 | naphthalene-naphthalene-phenyl substituted with 1-phenyl-benzimidazol-2-yl | phenyl | 4-pyridyl | 4-pyridyl |

TABLE-continued
| Number | R1 | R2 | Ar1 | Ar2 |
|---|---|---|---|---|
| 4-21 | 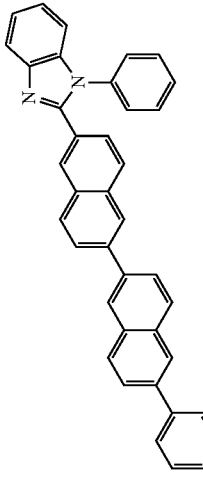 |  | 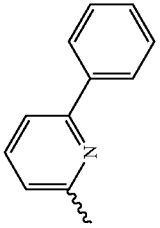 | 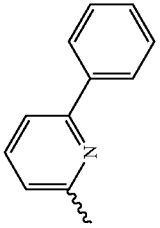 |
| 4-22 | 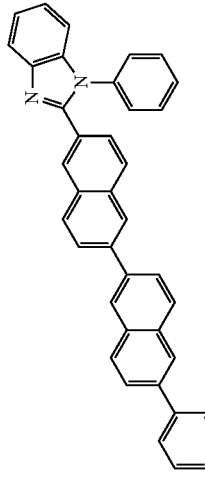 |  | 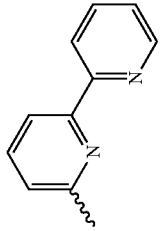 | 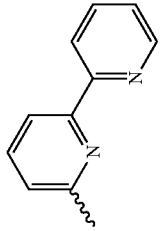 |
| 4-23 | 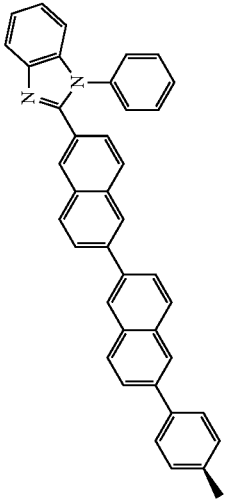 |  | 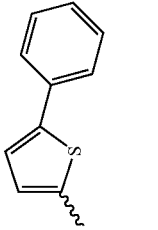 | 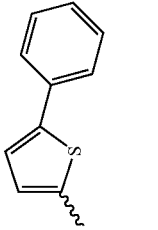 |
| 4-24 | 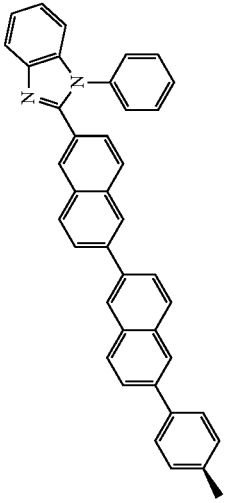 |  | 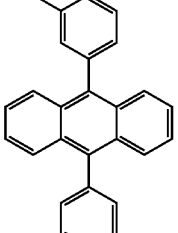 | 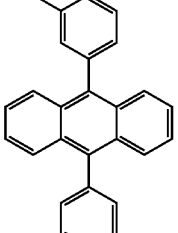 |

TABLE-continued

| Number | R1 | R2 | Ar1 | Ar2 |
|---|---|---|---|---|
| 5-1 | [structure] | [phenyl] | H | H |
| 5-2 | [structure] | [phenyl] | [phenyl] | [phenyl] |
| 5-3 | [structure] | [phenyl] | [biphenyl] | [biphenyl] |
| 5-4 | [structure] | [phenyl] | [naphthylphenyl] | [naphthylphenyl] |

TABLE-continued

| Number | R1 | R2 | Ar1 | Ar2 |
|---|---|---|---|---|
| 5-5 | | | | |
| 5-6 | | | | |
| 5-7 | | | | |
| 5-8 | | | | |

TABLE-continued

| Number | R1 | R2 | Ar1 | Ar2 |
|---|---|---|---|---|
| 5-9 | | | | |
| 5-10 | | | | |
| 5-11 | | | | |
| 5-12 | | | | |

TABLE-continued

| Number | R1 | R2 | Ar1 | Ar2 |
|---|---|---|---|---|
| 5-13 | | | | |
| 5-14 | | | | |
| 5-15 | | | | |
| 5-16 | | | | |

TABLE-continued

| Number | R1 | R2 | Ar1 | Ar2 |
|---|---|---|---|---|
| 5-17 | | | | |
| 5-18 | | | | |
| 5-19 | | | | |
| 5-20 | | | | |

TABLE-continued
| Number | R1 | R2 | Ar1 | Ar2 |
|---|---|---|---|---|
| 5-21 | 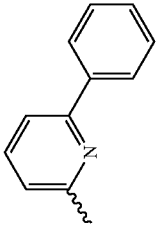 | 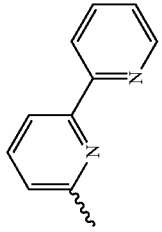 | 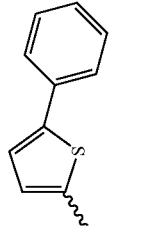 | 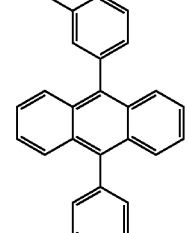 |
| 5-22 | 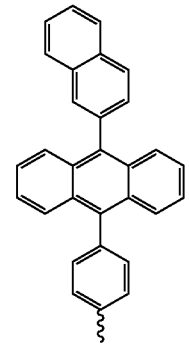 | 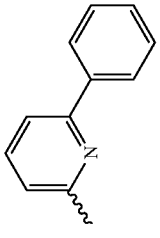 | 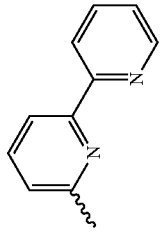 | 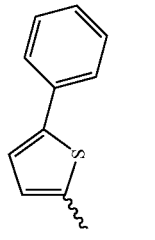 |
| 5-23 | 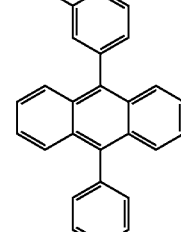 | 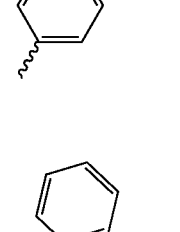 | 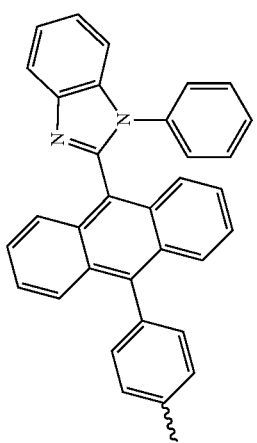 | 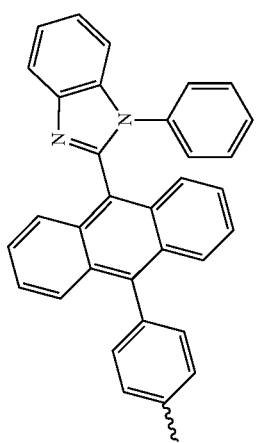 |
| 5-24 | 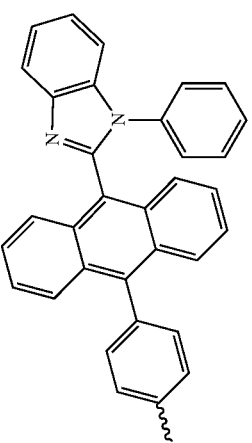 | 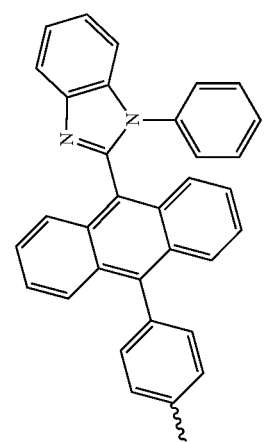 | 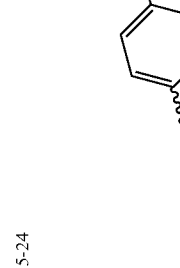 | |

TABLE-continued
| Number | R1 | R2 | Ar1 | Ar2 |
|---|---|---|---|---|
| 6-1 | 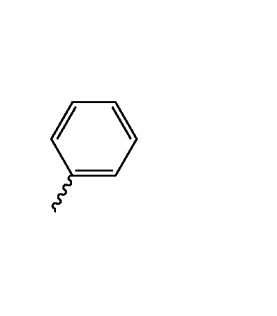 | 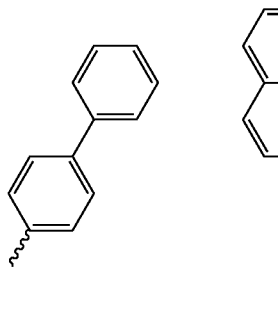 | H | H |
| 6-2 | 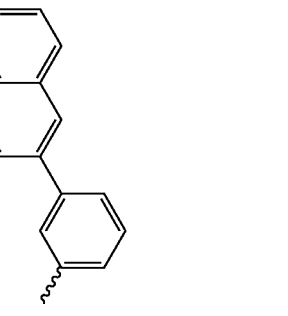 |  | 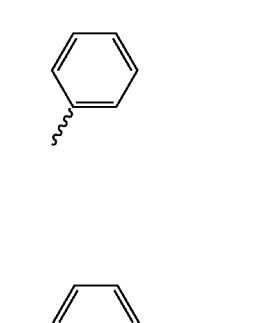 | 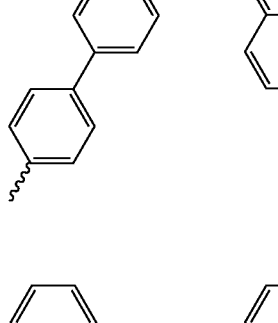 |
| 6-3 | 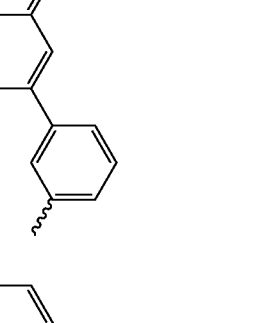 |  | 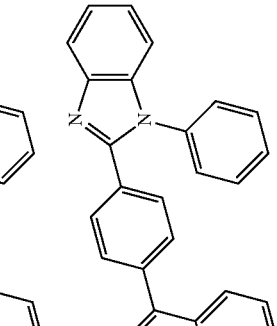 | 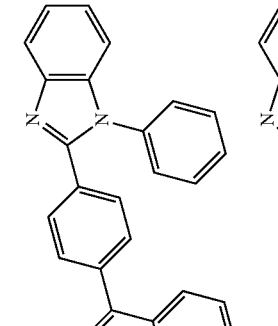 |
| 6-4 | 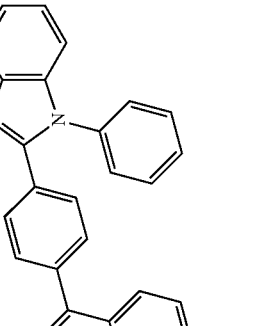 |  | 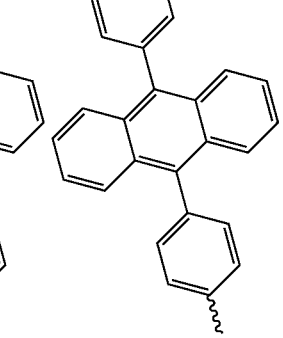 | 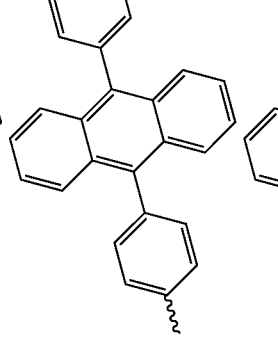 |

TABLE-continued
| Number | R1 | R2 | Ar1 | Ar2 |
|---|---|---|---|---|
| 6-5 |  | 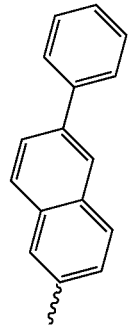 | 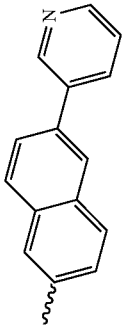 | 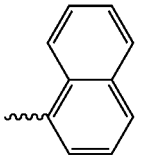 |
| 6-6 |  | 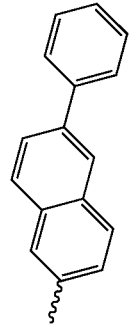 | 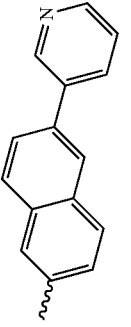 | 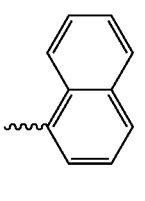 |
| 6-7 | 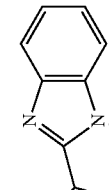 | 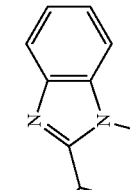 | 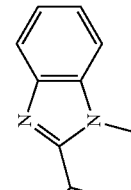 | 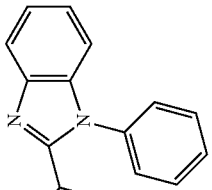 |
| 6-8 | 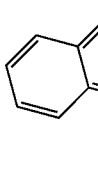 | 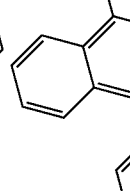 | 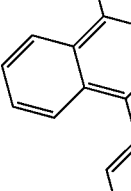 | 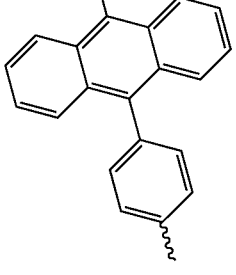 |

| Number | R1 | R2 | Ar1 | Ar2 |
|---|---|---|---|---|
| 6-9 | 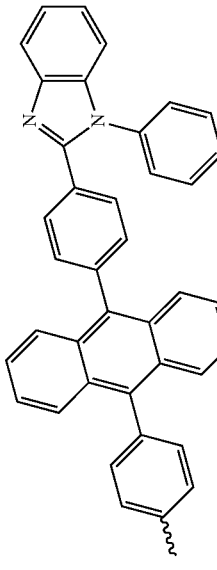 | 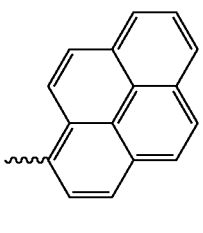 | 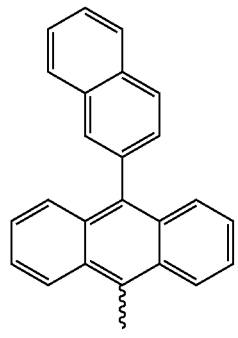 | 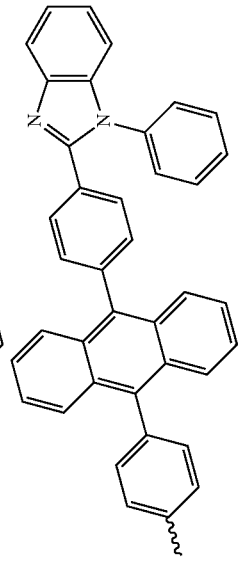 |
| 6-10 | 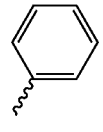 | 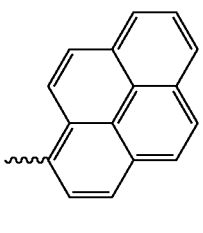 | 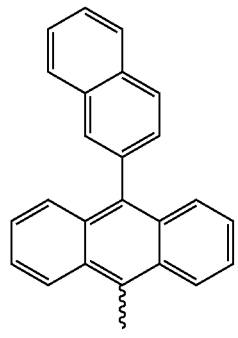 | 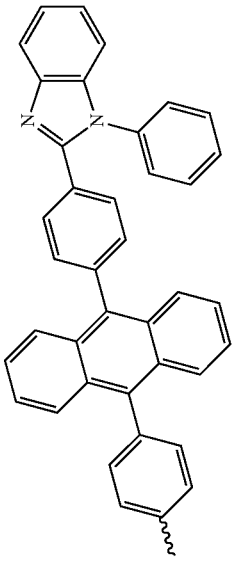 |
| 6-11 | 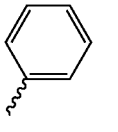 | 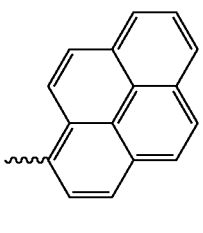 | 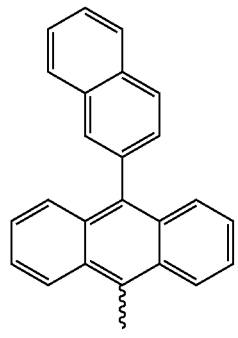 | 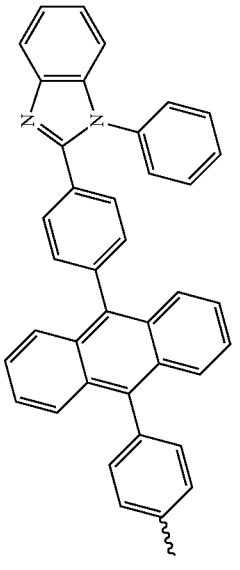 |
| 6-12 | 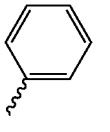 | 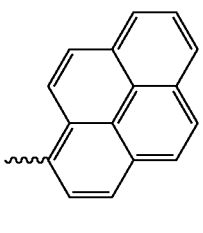 | 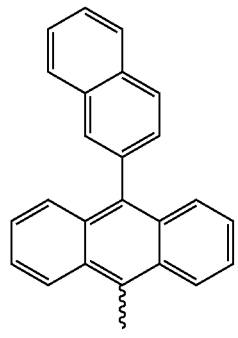 | |

TABLE-continued

| Number | R1 | R2 | Ar1 | Ar2 |
|---|---|---|---|---|
| 6-13 | | | | |
| 6-14 | | | | |
| 6-15 | | | | |
| 6-16 | | | | |

| Number | R1 | R2 | Ar1 | Ar2 |
|---|---|---|---|---|
| 6-17 | | | | |
| 6-18 | | | | |
| 6-19 | | | | |
| 6-20 | | | | |

TABLE-continued
| Number | R1 | R2 | Ar1 | Ar2 |
|---|---|---|---|---|
| 6-21 | 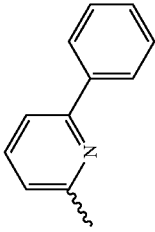 | 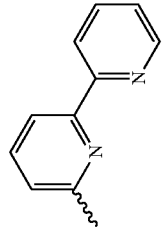 | 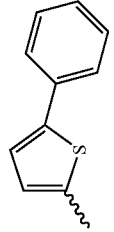 | 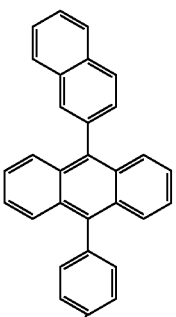 |
| 6-22 | 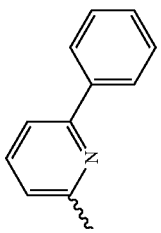 | 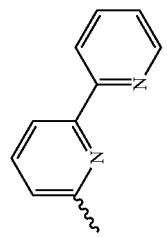 | 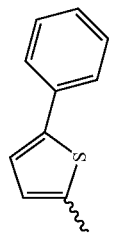 | 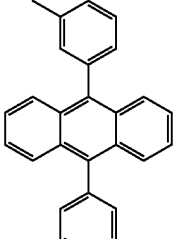 |
| 6-23 | 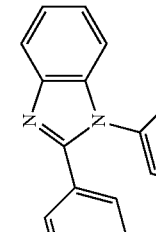 | 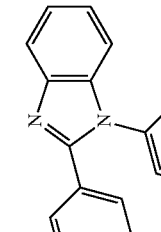 | 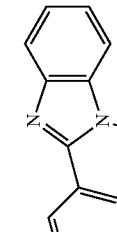 | 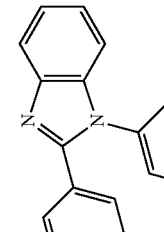 |
| 6-24 | 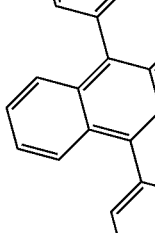 | 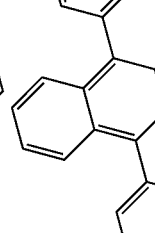 | 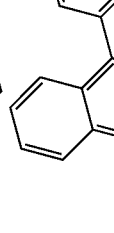 | 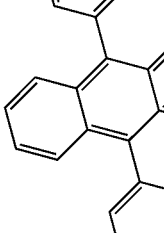 |
| 7-1 | 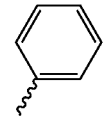 | H | H |  |

TABLE-continued

| Number | R1 | R2 | Ar1 | Ar2 |
|---|---|---|---|---|
| 7-2 | benzothiazole-phenyl | phenyl | phenyl | phenyl |
| 7-3 | benzothiazole-phenyl | phenyl | biphenyl | biphenyl |
| 7-4 | benzothiazole-phenyl | — | 2-naphthyl-phenyl | 2-naphthyl-phenyl |
| 7-5 | benzothiazole-phenyl | phenyl | naphthyl | naphthyl |
| 7-17 | benzothiazole-phenyl | phenyl | benzothiazole-phenyl | benzothiazole-phenyl |
| 7-18 | benzothiazole-phenyl | phenyl | benzothiazole-phenyl | benzothiazole-phenyl |
| 7-19 | benzothiazole-phenyl | phenyl | pyridyl | pyridyl |
| 7-20 | benzothiazole-phenyl | phenyl | pyridyl | pyridyl |

TABLE-continued
| Number | R1 | R2 | Ar1 | Ar2 |
|---|---|---|---|---|
| 7-21 | 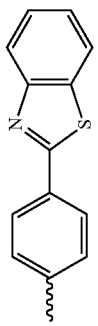 | 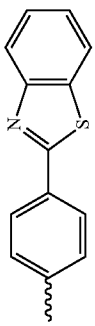 | 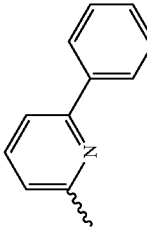 | 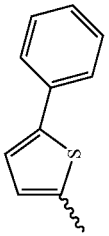 |
| 7-22 | 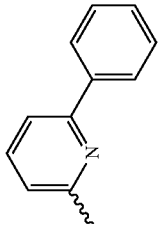 | 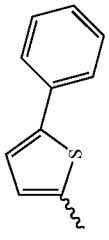 | 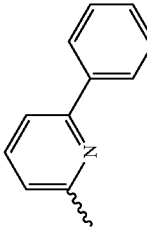 | 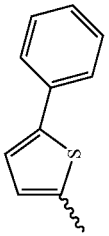 |
| 7-23 | 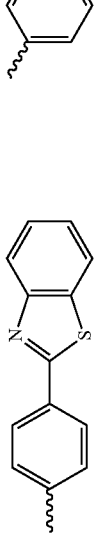 | 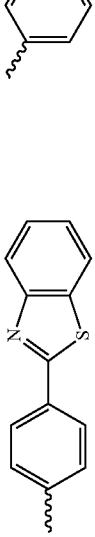 | 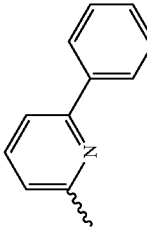 | 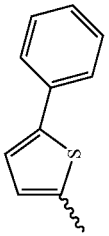 |
| 7-24 | 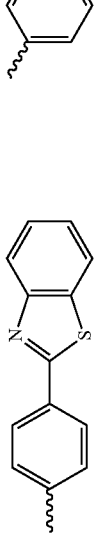 | 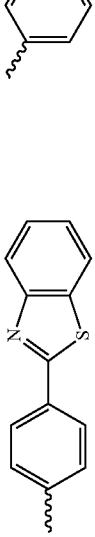 | 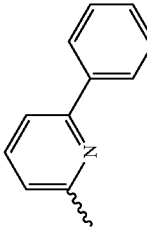 | 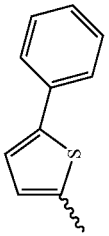 |

5. An organic electronic device comprising:
a first electrode;
a second electrode; and
one or more organic material layers which are interposed between the first electrode and the second electrode and include the compound according to any one of claims 1 to 4.

6. The organic electronic device as set forth in claim 5, wherein each of the organic material layers includes an electron injection layer, an electron transport layer, or the electron injection layer and the electron transport layer, and the electron injection layer, the electron transport layer, or the electron injection layer and the electron transport layer contain the compound according to any one of claims 1 to 4.

7. The organic electronic device as set forth in claim 5, wherein each of the organic material layers includes a light emitting layer, and the light emitting layer contains the compound according to any one of claims 1 to 4.

8. The organic electronic device as set forth in claim 5, wherein the organic electronic device is selected from the group consisting of an organic light emitting device, an organic solar cell, an organic photoconducting (OPC) drum, and an organic transistor.

* * * * *